(12) United States Patent
Adams et al.

(10) Patent No.: US 11,466,076 B2
(45) Date of Patent: Oct. 11, 2022

(54) BINDING DOMAIN OR ANTIBODY SPECIFIC TO A HUMAN SERUM ALBUMIN (HSA)

(71) Applicant: UCB BIOPHARMA SPRL, Brussels (BE)

(72) Inventors: Ralph Adams, Berkshire (GB); Sam Philip Heywood, Berkshire (GB)

(73) Assignee: UCB BIOPHARMA SRL, Brussels (BE)

( * ) Notice: Subject to any disclaimer, the term of this patent is extended or adjusted under 35 U.S.C. 154(b) by 556 days.

(21) Appl. No.: 16/098,085

(22) PCT Filed: Apr. 28, 2017

(86) PCT No.: PCT/EP2017/060266
§ 371 (c)(1),
(2) Date: Oct. 31, 2018

(87) PCT Pub. No.: WO2017/191062
PCT Pub. Date: Nov. 9, 2017

(65) Prior Publication Data
US 2019/0144529 A1 May 16, 2019

(30) Foreign Application Priority Data

May 1, 2016 (GB) .................................. 1607636
May 4, 2016 (GB) .................................. 1607828

(51) Int. Cl.
| | | |
|---|---|---|
| *C07K 16/00* | (2006.01) | |
| *C07K 16/18* | (2006.01) | |
| *C07K 14/76* | (2006.01) | |
| *C07K 14/765* | (2006.01) | |
| *C07K 16/06* | (2006.01) | |
| *A61K 39/395* | (2006.01) | |
| *A61K 39/00* | (2006.01) | |
| *C07K 16/46* | (2006.01) | |

(52) U.S. Cl.
CPC ............ *C07K 16/18* (2013.01); *C07K 16/464* (2013.01); *A61K 2039/505* (2013.01); *C07K 2317/24* (2013.01); *C07K 2317/33* (2013.01); *C07K 2317/34* (2013.01); *C07K 2317/55* (2013.01); *C07K 2317/56* (2013.01); *C07K 2317/565* (2013.01); *C07K 2317/567* (2013.01); *C07K 2317/92* (2013.01); *C07K 2317/94* (2013.01)

(58) Field of Classification Search
CPC .......... C07K 2317/31; C07K 2317/622; C07K 2317/24; C07K 2317/54; C07K 2317/35; C07K 2317/92; C07K 2317/76; C07K 2317/52; C07K 2317/55; C07K 2317/565; C07K 2319/10; C07K 2319/32; C07K 2319/33; C07K 2319/55; C07K 2319/75; C07K 2319/31; C07K 14/76; C07K 16/46; C07K 16/18; C07K 16/2809; A61K 2039/505; A61K 49/0058; A61P 25/00

See application file for complete search history.

(56) References Cited

U.S. PATENT DOCUMENTS 9,803,004 B2 * 10/2017 Adams .................... A61P 25/00
10,023,631 B2 * 7/2018 Adams .................... A61P 1/16

FOREIGN PATENT DOCUMENTS

| WO | 1991/009967 A1 | 7/1991 |
|---|---|---|
| WO | 1992/022853 A1 | 12/1992 |
| WO | 2005/003169 A2 | 1/2005 |
| WO | 2005/003170 A2 | 1/2005 |
| WO | 2005/003171 A2 | 1/2005 |
| WO | 2005/113605 A1 | 12/2005 |
| WO | 2009/040562 A1 | 4/2009 |
| WO | WO 2009/040562 A1 | 4/2009 |
| WO | 2010/035012 A1 | 4/2010 |
| WO | 2013/068571 A1 | 5/2013 |
| WO | 2013068571 A1 | 5/2013 |
| WO | 2014/096390 A1 | 6/2014 |
| WO | 2015/006337 A3 | 1/2015 |
| WO | WO 2015/006337 A2 | 1/2015 |
| WO | 2015/197772 A1 | 12/2015 |

OTHER PUBLICATIONS

Bowie et al. Science, 1990, 247:1306-1310.*
Pawson et al. 2003, Science 300:445-452.*
Burgess et al. J of Cell Bio. 1990, 111:2129-2138.*
Alaoui-Ismaili et al., Cytokine Growth Factor Rev. 2009; 20:501-507.*
Guo et al., PNAS 2004; 101:9205-9210.*
MacCallum et al.,J. Mol. Biol., 1996; 262: 732-745.*
Pascalis et al.,The Journal of Immunology, 2002; 169: 3076-3084.*
Casset et al., BBRC, 2003; 307: 198-205.*
Vajdos et al. ,J. Mol. Biol. 2002; 320: 415-428.*
Holm et al.,Mol. Immunol., 2007; 44: 1075-1084.*
Chen et al. ,J. Mol. Bio., 1999; 293: 865-881.*
Wu et al. ,J. Mol. Biol., 1999; 294:151-162.*
Rudikoff et al.,Proc. Natl. Acad. Sci. USA 1982 vol. 79: p. 1979.*
Adair and Lawson, "Therapeutic Antibodies," Drug Design Reviews—Online 2(3):209-217 (2005).
Andersen et al., "Extending half-life by indirect targeting of the neonatal Fc receptor (FcRn) using a minimal albumin binding domain" J Biol Chem 286: 5234-5241 (2011).
Angal et al., "A single amino acid substitution abolishes the heterogeneity of chimeric mouse/human (IgG4) antibody," Molecular Immunology 30:105-108 (1993).
Ascenzi and Fasano, "Allostery in a monomeric protein: The case of human serum albumin," Biophys Chem 148:16-22 (2010).

(Continued)

*Primary Examiner* — Chang-Yu Wang
(74) *Attorney, Agent, or Firm* — Medler Ferro Woodhouse & Mills

(57) ABSTRACT

The present disclosure relates to a method of modulating the half-life of a binding domain specific to a serum carrier protein by mutating the sequence and a modulated binding domain specific to a serum carrier protein.

12 Claims, 7 Drawing Sheets

Figure 2:
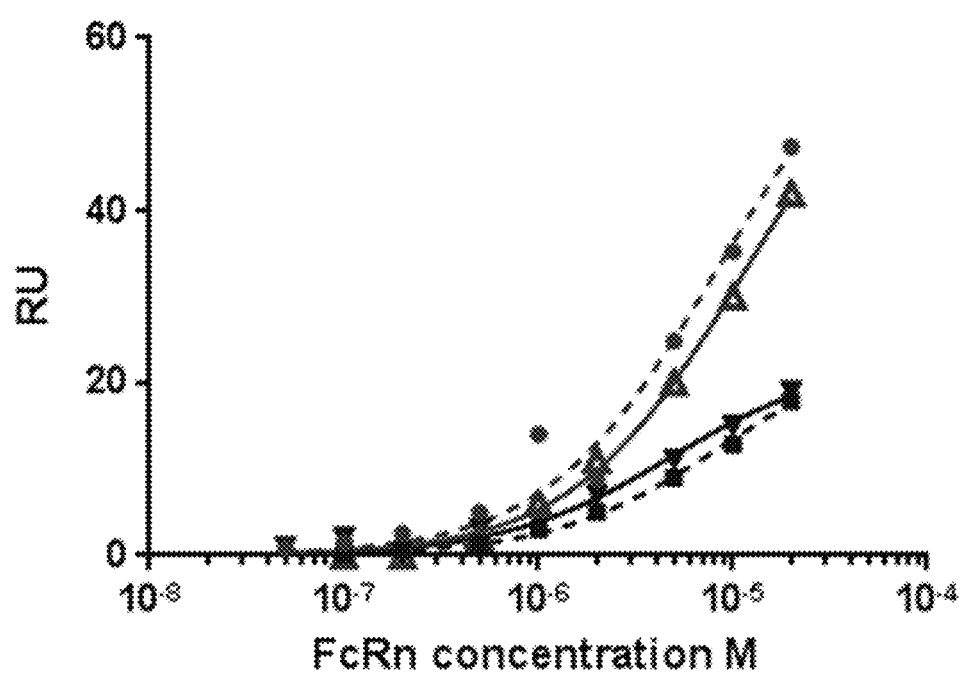

Specification includes a Sequence Listing.

(56) References Cited

OTHER PUBLICATIONS

Bal et al., "Binding of transition metal ions to albumin: Sites, affinities and rates," Biochim Et Biophys Act 1830(12):5444-5445 (2013).
Brünger et al., "Crystallography & NMR system: A new software suite for macromolecular structure determination," Acta Crystallogr D Biol Crystallogr; 54 (Pt 5):905-21 (1998).
Brünger, "Version 1.2 of the Crystallography and NMR system," Nature Protocols 2:2728-2733 (2007).
Cain et al., "CHO cell line engineered to express XBP1 and ERO1-Lα has increased levels of transient protein expression," Biotechnol Prog 29:697-706 (2013).
Chaudhury et al., "The major histocompatibility complex-related Fc receptor for IgG (FcRn) binds albumin and prolongs its lifespan," J Exp Med 197: 315-322 (2003).
Chen, "MolProbity: all-atom structure validation for macromolecular crystallography," Acta Crystallogr D Biol Crystallogr D66:12-21 (2010).
Chothia and Lesk, "Canonical structures for the hypervariable regions of immunoglobulins," J. Mol. Biol., 196(4):901-917 (1987).
Clargo et al., "The rapid generation of recombinant functional monoclonal antibodies from individual, antigen-specific bone marrow-derived plasma cells isolated using a novel fluorescence-based method," MAbs; 6:143-159 (2014).
Curry, "Lessons from the crystallographic analysis of molecule binding to Human Serum Albumin," Drug Metab Pharmacokinet 24(4):342-357 (2009).
Curry et al., "Crystal structure of human serum albumin complexed with fatty acid reveals an asymmetric distribution of binding sites," Nat Struct Biol 5:827-835 (1998).
Dennis et al., "Albumin binding as a general strategy for improving the pharmacokinetics of proteins," J Biol Chem 277:35035-35043 (2002).
Elsadek and Kratz, "Impact of albumin on drug delivery—New applications on the horizon," J Control Release 157:4-28 (2012).
Emsley and Cowtan, "Coot: model-building tools for molecular graphics" Acta Crystallogr D Biol Crystallogr. D60:2126-32 (2004).
Evans, "Scaling and assessment of data quality," P. Acta Cryst. (2006) D62:72-82.
Flanagan and Jones, "Fab antibody fragments," Drug Safety 27:1115-1133 (2004).
Ghuman et al., "Structural basis of the drug-binding specificity of human serum albumin," J Mol Biol 353:38-52 (2005).
Harris, "Processing of C-terminal lysine and arginine residues of proteins isolated from mammalian cell culture," Journal of Chromatography 705:129-134 (1995).
Holliger and Hudson, "Engineered antibody fragments and the rise of single domains," Nature Biotech. 23(9):1126-1136 (2005).
Holt et al., Anti-serum albumin domain antibodies for extending the half-lives of short-lived drugs. Protein Eng Des Sel 21(5):283-288 (2008).
Hopp et al., "The effects of affinity and valency of an albumin-binding domain (ABD) on the half-life of a single-chain diabody-ABD fusion protein," Protein Eng Des Sel 23:827-834 (2010).
International Search Report issued in PCT/EP2017/060266, dated Sep. 13, 2017.
Junghans and Anderson, "The protection receptor for IgG catabolism is the beta2-microglobulin-containing neonatal intestinal receptor," Proc Natl Acad Sci USA 93: 5512-5516 (1996).
Kabsch, "XDS," Acta Cryst D66:125-132 (2010).

Kontermann, "Strategies for extended serum half-life of protein therapeutics," Curr Opin Biotechnol 22:868-876 (2011).
Leslie, "The integration of macromolecular diffraction data," Acta Cryst. D62:48-57 (2006).
Leslie and Powell, "Processing diffraction data with mosflm," In: Read R.J., Sussman J.L. (eds) Evolving Methods for Macromolecular Crystallography. NATO Science Series, vol. 245:45-51 (2007).
Lightwood et al., "Antibody generation through B cell panning on antigen followed by in situ culture and direct RT-PCR on cells harvested en masse from antigen-positive wells," J Immunol Methods 316:133-143 (2006).
Majorek et al., "Structural and immunologic characterization of bovine, horse, and rabbit serum albumins," Mol Immunol 52:174-182 (2012).
McCoy, "Phaser crystallographic software," J Appl Cryst 40:658-674 (2007).
Müller et al., "Improved pharmacokinetics of recombinant bispecific antibody molecules by fusion to human serum albumin," J Biol Chem 282:12650-12660 (2007).
Nguyen et al., "The pharmacokinetics of an albumin-binding Fab (AB.Fab) can be modulated as a function of affinity for albumin," Protein Eng Des Sel 9:291-297 (2006).
O'Connor-Semmes et al., "GSK2374697, a novel albumin-binding domain antibody (AlbudAb), extends systemic exposure of exendin-4: first study in humans-PK/PD and safety," Clin Pharmacol Ther 96:704-712 (2014).
Oganesyan et al, "Structural insights into neonatal Fc receptor-based recycling mechanisms," J Biol Chem 289: 7812-7824 (2014).
Sleep et al., "Albumin as a versatile platform for drug half-life extension," Biochim Biophys Acta 1830(12):5526-5534 (2013).
Smith et al. "Prolonged in vivo residence times of antibody fragments associated with albumin," Bioconjug Chem 12:750-756 (2001).
Sørensen et al., "Insulin detemir is a fully efficacious, low affinity agonist at the insulin receptor," Diabetes Obes Metab 12:655-673 (2010).
Tickle et al., "High-throughput screening for high affinity antibodies," J Lab Auto 14(5): 303-307 (2009).
Tijink et al., "Improved tumor targeting of anti-epidermal growth factor receptor Nanobodies through albumin binding: taking advantage of modular Nanobody technology," Mol Cancer Ther 8: 2288-2297 (2008).
Trüssel et al., "New strategy for the extension of the serum half-life of antibody fragments," Bioconjug Chem 20:2286-2292 (2009).
Van Roy et al., "The preclinical pharmacology of the high affinity anti-IL-6R Nanobody® ALX-0061 supports its clinical development in rheumatoid arthritis," Arthritis Research & Therapy 17(1):135 (2015).
Verma et al., "Antibody engineering: comparison of bacterial, yeast, insect and mammalian expression systems," Journal of Immunological Methods 216:165-181 (1998).
Holt et al., "Anti-serum albumin domain antibodies for extending the half-lives of short Tived drugs," *Protein Engineering, Selection & Design* 21(5):283-288 (2008).
Kontermann, "Strategies for extended serum half-life of protein therapeutics," *Current Opinion in Biotechnology* 22(6):868-876 (2011).
Tickle et al., "High-Throughput Screening for High Affinity Antibodies," *Journal of the Association for Laboratory Automation* 14(5):303-307 (2009).
Bakheet Elsadek et al., "Impact of albumin on drug delivery—New applications on the horizon," Journal of Controlled Release 157(1):4-28 (2012).

\* cited by examiner

FIGURE 1

(a) CA645 Heavy chain sequence alignment

```
                  1         10        20        30        40
CA645 VH          -QSLEESGGRLVTPGTPLTLTCTVS GIDLSNYAIN WVRQAPGKGLEWIG
                   *** *     *   *  ** * * **                       **
VH3 1-3 3-23      EVQLLESGGGLVQPGGSLRLSCAAS            WVRQAPGKGLEWVS gH1               EVQLLESGGGLVQPGGSLRLSCAVS GIDLSNYAIN WVRQAPGKGLEWIG
gH5               EVQLLESGGGLVQPGGSLRLSCAVS GIDLSNYAIN WVRQAPGKGLEWIG 50        60        70        80        90
CA645 VH          IIWASGTTFYATWAKG RFTISRPST--TVDLEMTSLTTADTATYFCAR
                                    *****  ** *  *   ***    *  *   *
VH3 1-3 3-23                       RFTISRDNSKNTLYLQMNSLRAEDTAVYYCAK gH1               IIWASGTTFYATWAKG RFTISRDST--TVYLQMNSLRAEDTAVYYCAR
gH5               IIWASGTTFYATWAKG RFTISRDNSKNTVYLQMNSLRAEDTAVYYCAR 100       110
CA645 VH          TVPGYSTAPYFDL WGPGTLVTVSS
                                 *
JH4                          YFDY WGQGTLVTVSS gH1               TVPGYSTAPYFDL WGQGTLVTVSS
gH5               TVPGYSTAPYFDL WGQGTLVTVSS
```

(b) CA645 Light chain sequence alignment

```
                  1         10        20        30        40
CA645 VL          AAVLTQTPSPVSAAVGGTVTINC QSSPSVWSNFLS WYQQKPGQPPKLLIY
                   ****   *    *   **   *                           **
VκI 2-1-(1) L5    DIQMTQSPSSVSASVGDRVTITC              WYQQKPGKAPKLLIY gL1               DIVMTQSPSSVSASVGDRVTITC QSSPSVWSNFLS WYQQKPGKAPKLLIY
gL4               DIQMTQSPSSVSASVGDRVTITC QSSPSVWSNFLS WYQQKPGKAPKLLIY 50        60        70        80        90
CA645 VL          EASKLTS GVPSRFKGSGSGTQFTLTISDVQCGDAATYYC GGGYSSISD
                           *         *       ** ** *
VκI 2-1-(1) L5            GVPSRFSGSGSGTDFTLTISSLQPEDFATYYC gL1               EASKLTS GVPSRFKGSGSGTDFTLTISSLQPEDFATYYC GGGYSSISD
gL4               EASKLTS GVPSRFSGSGSGTDFTLTISSLQPEDFATYYC GGGYSSISD

100
CA645 VL          TTFGGGTKVVVK
                    **
Jκ4               LTFGGGTKVEIK gL1               TTFGGGTKVEIK
gL4               TTFGGGTKVEIK
```

Figure 7

SEQ ID NO: 1 CA645 VH

QSLEESGGRLVTPGTPLTLTCTVSGIDLSNYAINWVRQAPGKGLEWIGIIWASGTTFYATWAKG
RFTISRPSTT VDLEMTSLTTADTATYFCARTVPGYSTAPYFDLWGPGTLVTVSS

SEQ ID NO: 2 CA645 VH gH1

EVQLLESGGGLVQPGGSLRLSCAVSGIDLSNYAINWVRQAPGKGLEWIGIIWASGTTFYATWAKG
RFTISRDSTT VYLQMNSLRAEDTAVYYCARTVPGYSTAPYFDLWGQGTLVTVSS

SEQ ID NO: 3 CA645 VH gH5

EVQLLESGGGLVQPGGSLRLSCAVS GIDLSNYAIN WVRQAPGKGLEWIG IIWASGTTFYATWAKG
RFTISRDNSKNTVYLQMNSLRAEDTAVYYCAR TVPGYSTAPYFDL WGQGTLVTVSS

SEQ ID NO: 4 CA645 VH gH37

EVQLLESGGGLVQPGGSLRLSCAVSGIDLSNYAINWVRQAPGKGLEWIGIIWASGTTAYATWAKGRFTI
SRDNSKNTV YLQMNSLRAEDTAVYYCARTVPGYSTAPYFDLWGQGTLVTVSS

SEQ ID NO: 5 CA645 VH gH47

EVQLLESGGGLVQPGGSLRLSCAVS GIDLSNYAIN WVRQAPGKGLEWIG IIWASGTTFYATWAKG
RFTISRDNSKNTVYLQMNSLRAEDTAVYYCAR TVPGYSAAPYFDL WGQGTLVTVSS

SEQ ID NO: 6 CA645 VL

AAVLTQTPSPVSAAVGGTVTINCQSSPSVWSNFLSWYQQKPGQPPKLLIYEASKLTS
GVPSRFKGSGSGTQFTLTISDVQCGDAATYYCGGGYSSISDTTFGGGTKVVVK

SEQ ID NO: 7 CA645 VL gL1

DIVMTQSPSSVSASVGDRVTITCQSSPSVWSNFLSWYQQKPGKAPKLLIYEASKLTS
GVPSRFKGSGSGTDFTLTISSLQPEDFATYYCGGGYSSISDTTFGGGTKVEIK

SEQ ID NO: 8 CA645 VL gL4

DIQMTQSPSSVSASVGDRVTITC QSSPSVWSNFLS WYQQKPGKAPKLLIY EASKLTS
GVPSRFSGSGSGTDFTLTISSLQPEDFATYYC GGGYSSISD TTFGGGTKVEIK

Figure 7 continued

SEQ ID NO: 9 CA645 VL gL5

DIQMTQSPSSVSASVGDRVTITC <u>QSSPSVASNFLS</u> WYQQKPGKAPKLLIY <u>EASKLTS</u>
GVPSRFSGSGSGTDFTLTISSLQPEDFATYYC <u>GGGYSSISD</u> TTFGGGTKVEIK

BINDING DOMAIN OR ANTIBODY SPECIFIC TO A HUMAN SERUM ALBUMIN (HSA)

The present disclosure relates to a method modulating the half-life of a binding domain specific to a serum carrier protein by mutating the sequence and a modulated binding domain specific to a serum carrier protein.

BACKGROUND

Increasing the serum half-life of biological drugs by targeting serum protein carriers, for example human serum albumin (HSA) is now well established[1,2]. HSA is utilized because it's half-life is 19 days. It is the most abundant protein in blood serum (34-54 g/L), and is widely distributed in tissues.[3] Therefore, it is a target that is readily available and safe for binding, particularly as such a small percentage of the total albumin is utilized in this approach.

Of the serum proteins, only IgG has a similarly long half-life (21 days). The long serum half-lives of HSA and IgG are primarily due to protection from intracellular lysosomal degradation by the neonatal Fc receptor (FcRn).[4,5] FcRn recycles HSA and IgG back to the cell surface following non-specific pinocytosis of plasma into vesicles by endothelial cells and hematopoietic cells lining the vascular space. The pinocytotic vesicles acidify by fusion with the early endosome enabling HSA and IgG to bind to FcRn in a pH dependent manner. Vesicles bearing membrane receptors, including FcRn, and bound HSA and IgG, are recycled back to the cell surface whilst the remaining unbound material is channeled to the lysosome for degradation. HSA and IgG bind weakly to FcRn at neutral pH and so are released back into the circulation when the recycled vesicles are exposed to the neutral pH of the blood.[2]

HSA can be exploited in one of two ways. One approach is to directly couple the therapeutic protein to HSA, either genetically or chemically.[6,7] A second approach is to use an albumin binding domain. Examples of binding domains used to date include fatty acids (myristic acid),[8] organic molecules (Albutag),[9] synthetic peptides,[10,11] bacterial albumin binding domains (Albumod™),[12,13] single domain antibodies (Nanobody™, AlbudAb™)[14-17] and a Fab.[18]

Figure 3:
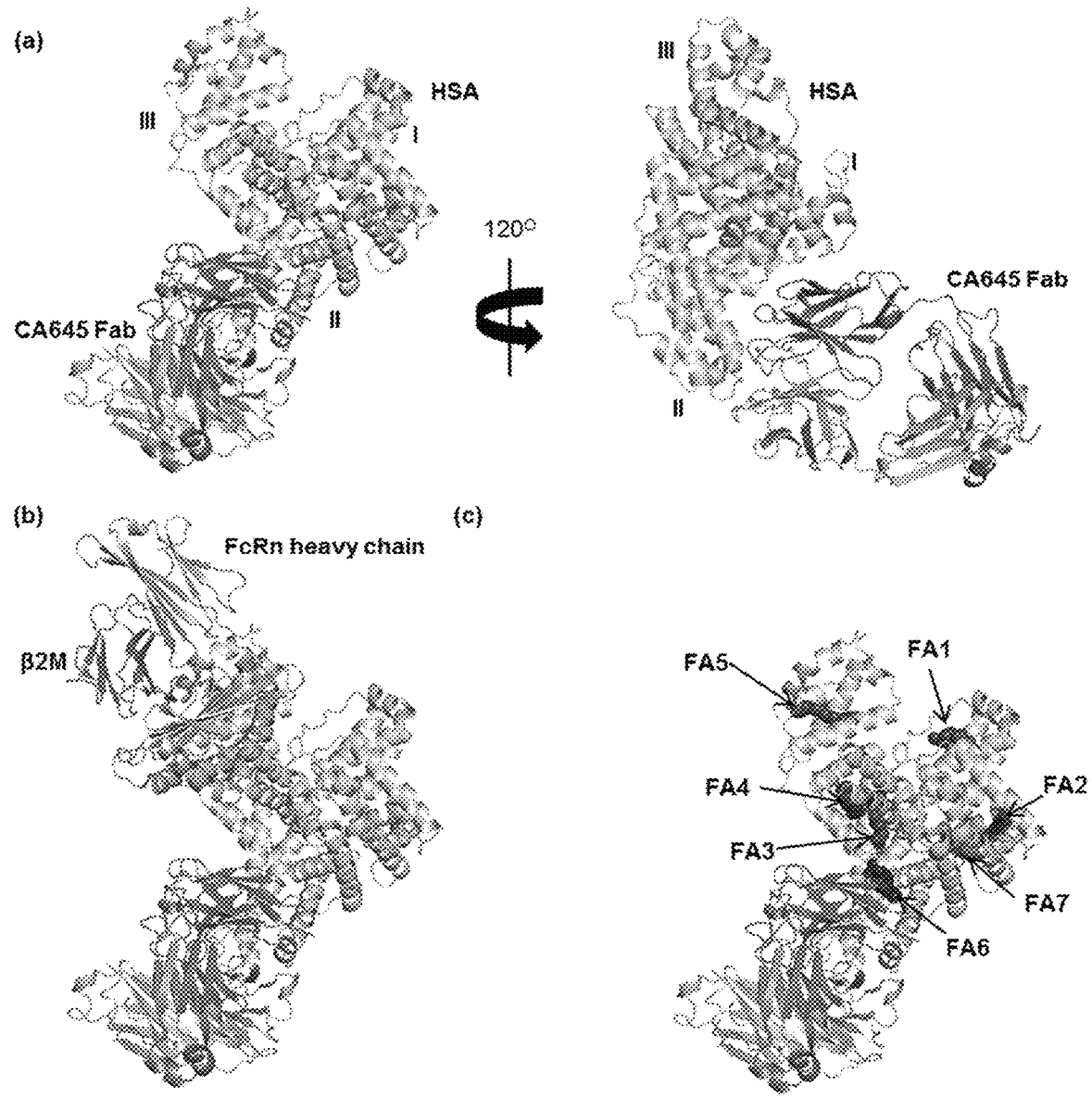

Nguyen et al 2006 investigated the half-life of Fab fragments linked to a C-terminal albumin binding peptide. Nguyen concluded that reduced affinity for albumin correlated with a reduced half-life and higher rates of clearance. FIG. 3 therein suggests the relationship is almost linear. This paper also went on to say that a very small difference in the fraction of the antibody that is unbound in vivo will have a profound effect on the rate of clearance.

The present inventors have investigated the correlation between the affinity of binding domains comprising a VH and VL specific to a serum protein carrier and the in vivo half-life of the same. They have established that the duration of the half-life for binding domains is more complicated than the response for albumin binding peptides, in that large reductions in the observed affinity often translate to a moderate reduction in half-life and in some instances reduced affinity can lead to increases in half-life, which is counter-intuitive.

SUMMARY OF THE DISCLOSURE

Thus there is provided a binding domain comprising a VH and VL specific to a serum carrier protein wherein the domain is mutated by a modification in the light chain variable domain (VL), in the heavy chain variable domain (VH) and a combination thereof, and the mutated binding domain has a half-life which is higher or lower than the half-life for the unmutated binding domain, for example with the proviso that the mutation is other than a mutation consisting of I50A, T56A, T95A, V96A, P97A, G98A, Y99A, S100A, T100Aa, Y100Ca, I50A and T95A, I50A and G98A, I50A and Y99A, T56A and T95A, T56A and G98A, and T56A and Y99A of SEQ ID NO: 1.

Thus there is provided a binding domain comprising a VH and VL specific to a serum carrier protein wherein the domain is mutated by a modification selected from one or two amino acids substitutions in the light chain variable domain (VL), one or two mutations in the heavy chain variable domain (VH) and a combination thereof, and the mutated binding domain has a half-life which is higher or lower than the half-life for the unmutated binding domain, for example with the proviso that the mutation is other than a mutation consisting of I50A, T56A, T95A, V96A, P97A, G98A, Y99A, S100A, T100Aa, Y100Ca, I50A and T95A, I50A and G98A, I50A and Y99A, T56A and T95A, T56A and G98A, and T56A and Y99A of SEQ ID NO: 1.

In one embodiment the serum carrier protein is selected from, for example thyroxine-binding protein, transthyretin, α1-acid glycoprotein, transferrin, fibrinogen and albumin, or a fragment of any thereof, such as albumin, in particular human serum albumin.

In one embodiment the binding domain is specific to domain II of albumin.

In one embodiment the mutation is a modification in the VL, for example wherein the mutation is substitution of one or two amino acids in the VL, such as a modification/substitution in a CDR selected from L1, L2, L3 and a combination thereof, in particular wherein the CDR is L1.

In one embodiment the mutated amino acid(s) in CDR L1 is/are independently selected from a position 26, 27, 28, 29, 30, 31, 32, 33, 34 and 35, such as position 30.

In one embodiment the amino acid(s) at the relevant position(s) in VL is/are replaced by a hydrophobic residue, for example selected from alanine, isoleucine, phenylalanine, valine, proline, and glycine, such as alanine.

In one embodiment the mutations consist of modifications to the VL. Surprisingly the present inventors have established that modifications in the VL can be made which increase the Kd of the binding domain and reduces the affinity of the binding domain but increases the half-life of the molecule.

In one embodiment the mutation(s) is/are in the VH domain, for example the mutation is substitution of one or two amino acids in the VH, such as mutation in a CDR selected from H1, H2, H3 and combinations thereof, in particular wherein the CDR is H2 and/or H3, more specifically wherein the CDR is H2.

In one embodiment the mutated amino acid(s) in CDR H2 is/are independently selected from a position 50, 51, 52, 53, 54, 55, 56, 57, 58, 59, 60, 61, 62, 63, 64, 65 and combinations thereof, which for example is/are replaced by a hydrophobic residue, in particular independently selected from alanine, isoleucine, phenylalanine, valine, proline, and glycine, such as alanine.

In one embodiment the mutated amino acid(s) is/are in CDR is H3, and in particular the mutated amino acid(s) is/are independently selected from a position 95, 96, 97, 98, 99, 100, 101, 102, 103, 104, 105, 106 or 107, more specifically the residue 101 is mutated.

In one embodiment the amino acid at the relevant position(s) in CDR H3 is replaced by a hydrophobic residue, for example independently selected from alanine, isoleucine, phenylalanine, valine, proline, and glycine, such as alanine.

In one or more embodiments the one or more amino acid substitution(s) is/are a non-conservative amino acid substitution, for example wherein the non-conserved amino acid is a selection from the natural amino acids alanine, valine, isoleucine, leucine, methionine, phenylalanine, tyrosine, tryptophan, threonine, asparagine, glutamine, glycine, proline, arginine, lysine, aspartic acid and glutamic acid.

In one embodiment the binding domain comprises a CDR grafted variable domain.

In one embodiment the binding domain is humanised, for example the binding domain comprises a human framework in the VH and/or VL.

In one embodiment the VH framework is human (for example VH3, such as VH3 1-3 3-23) and comprises 1, 2, 3, 4, 5 or 6 amino acid substitutions, such as amino acids which are donor residues.

In one embodiment the VH comprises a sequence selected from SEQ ID NO: 2, 3, 4 and 5 or a variant of any one of the same with at least 95, 96, 97, 98 or 99% similarity or identity, such as a sequence shown in SEQ ID NO: 2, 3, 4, 5 or 6 (particularly 5 or 6).

In one embodiment the VL framework is human (for example Vκ1, such as 2-1-(1) L5), for example comprising 1, 2 or 3 amino acid substitutions, such as amino acids which are donor residues.

In one embodiment the VL domain comprises a sequence selected from SEQ ID NO: 6, 7, 8 and 9 or a variant of any one of the same with at least 95, 96, 97, 98 or 99% similarity or identity.

In one embodiment the VH and VL sequences are selected from the combinations SEQ ID NO:2 & 6, 2 & 7, 2 & 8, 2 & 9, 3 & 6, 3 & 7, 3 & 8, 3 & 9, 4 & 6, 4 & 7, 4 & 8, 4 & 9, 5 & 6, 5 & 7, 5 & 8 and 5 & 9 or a variant or variants of any of the same with at least 95, 96, 97, 98 or 99% similarity or identity, in particular the VL and VH sequences are SEQ ID NO: 9 and SEQ ID NO: 3, respectively, or the VL and VH sequences are SEQ ID NO: 8 and SEQ ID NO: 4 respectively, or the VL and VH sequences are SEQ ID NO: 9 and SEQ ID NO: 5, respectively, or the VL and VH sequences are SEQ ID NO: 9 and SEQ ID NO: 4.

In one embodiment the binding domain is human.

In one embodiment, the affinity of the binding partners is high, 5 nM or stronger, such as 900, 800, 700, 600, 500, 400, 300, 200, 100, 50, or 10 pM or stronger.

In one embodiment provided is an antibody molecule comprising a binding domain according to the present disclosure, in particular a multispecific antibody molecule, such as a bispecific.

In one embodiment there is provided a pharmaceutical composition comprising a binding domain according to the present disclosure or an antibody molecule described herein.

In a further aspect there is provided a method of treating a patient comprising administering a therapeutically effect amount of a binding domain according to the present disclosure, an antibody molecule described herein, or a pharmaceutical composition comprising any one of the same.

Also provided is a binding domain according to the present disclosure, an antibody molecule described herein, or a pharmaceutical composition comprising any one of the same, for use in treatment.

In one embodiment there is provided a binding domain according to the present disclosure, an antibody molecule described herein or a pharmaceutical composition comprising any one of the same for use in treatment, in particular the treatment of selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis, hypochlorhydia and cancer, including breast cancer, lung cancer, gastric cancer, ovarian cancer, hepatocellular cancer, colon cancer, pancreatic cancer, esophageal cancer, head & neck cancer, kidney, and cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof.

Use of a binding domain according to the present disclosure, an antibody molecule described herein, or a pharmaceutical composition comprising the same, in the manufacture of a medicament, for example for the treatment of selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis, hypochlorhydia and cancer, including breast cancer, lung cancer, gastric cancer, ovarian cancer, hepatocellular cancer, colon cancer, pancreatic cancer, esophageal cancer, head & neck cancer, kidney, and cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof.

In an independent aspect there is provided a method of selecting a serum protein carrier binding domain to provide a bespoke half-life comprising the steps of: providing a panel of VH/VL pairs specific to said serum protein carrier, and analysing a half-life thereof in vivo, and selecting a domain which most closely matches the half-life required for a biological molecule comprising the domain in a human subject.

In one embodiment the serum carrier protein is selected from thyroxine-binding protein, transthyretin, α1 glycoprotein, transferrin, fibrinogen and albumin, or a fragment of any thereof, for example albumin, such as human serum albumin.

In one aspect the panel of VH/VL pairs is prepared by mutating a variable domain in a parent antibody.

In one embodiment the mutation is at least one modification to the VL, for example wherein the VL modification is selected from one or two amino acids substitutions in the light chain variable domain (VL) and the mutated binding domain has a half-life which higher or lower than the half-life for the unmutated binding domain.

In one embodiment the mutation in VL is a mutations in CDR L1, CDRL2, and/or CDRL3, in particular CDR L2 or CDR L3.

In one embodiment the mutation(s) in the binding domain consists of a modification or modifications to the VL domain.

In one embodiment the mutation is at least one modification to the VH.

In one embodiment the mutation is one or two mutations in the heavy chain variable domain (VH), wherein the mutated binding domain has a half-life which higher or lower than the half-life for the unmutated binding domain (also referred to herein as parent antibody).

In one embodiment a mutation(s) is in CDR H1, CDRH2, and/or CDRH3, in particular CDR H2 or CDR H3.

In one embodiment the method according to the disclosure further comprises the step of replacing histidine residues in a VH and/or VL (from the panel or for the panel) with an alternative amino acid residue.

In one embodiment the method further comprises the step of assessing the properties of one or more binding domains, at two or more biologically relevant pH's, such as about pH 5 and pH7.

In one embodiment the mutations increase the numerical value of the Kd.

In one embodiment there is provided a method wherein the affinity is increased.

In one embodiment there is provided a method wherein the affinity is decreased.

In one embodiment a crystal structure of the serum carrier protein with an antibody such as the parent antibody is employed in deciding which residues to modify/mutate.

In one independent aspect there present disclosure provides a method describes in the paragraphs below:

1. A method of selecting a serum protein carrier binding domain to provide a bespoke half-life comprising the steps of: providing a panel of VH/VL pairs specific to said serum protein carrier, and
analysing a half-life thereof in vivo, and
selecting a domain which most closely matches the half-life required for a biological molecule comprising the domain in a human subject.
2. A method according to paragraph 1, wherein the serum carrier protein is selected from thyroxine-binding protein, transthyretin, α1-acid glycoprotein, transferrin, fibrinogen and albumin, or a fragment of any thereof.
3. A method according to paragraph 2, wherein the serum protein carrier is albumin.
4. A method according to paragraph 3, wherein the albumin is human serum albumin.
5. A method according to any one of paragraphs 1 to 4, wherein the panel of VH/VL pairs is prepared by mutating a variable domain in a parent antibody.
6. A method according to paragraph 5, wherein the mutation is at least one modification to the VL.
7. A method according to paragraph 6, wherein the VL modification is selected from one or two amino acids substitutions in the light chain variable domain (VL) and the mutated binding domain has a half-life which higher or lower than the half-life for the unmutated binding domain.
8. A method according to any one of paragraphs 5 to 7, wherein a mutations is in CDR L1, CDRL2, and/or CDRL3, in particular CDR L2 or CDR L3.
9. A method according to any one of paragraphs 5 to 8, wherein the mutation consists of a modification or modifications to the VL domain.
10. A method according to any one of paragraphs 1 to 8, wherein the mutation is at least one modification to the VH.
11. A method according to paragraphs 9, wherein the mutation is one or two mutations in the heavy chain variable domain (VH) and a combination thereof, and the mutated binding domain has a half-life which higher or lower than the half-life for the unmutated binding domain.
12. A method according to paragraphs 10 or 11, wherein a mutation(s) is in CDR H1, CDRH2, and/or CDRH3, in particular CDR H2 or CDR H3.
13. A method according to any one of paragraphs 1 to 12, which further comprises the step of replace histidine residues in a VH and/or VL employed in the panel with an alternative amino acid residue.
14. A method according to any one of paragraphs 1 to 13, which further comprises the step of assessing the properties of one or more binding domains, at two or more biologically relevant pH's, such as about pH 5 and pH7.
15. A method according to any one of paragraphs 1 to 14, where the mutation(s) increases the numerical value of the Kd.
16. A method according to any one paragraphs 1 to 15, wherein the affinity increased.
17. A method according to any one of paragraphs 1 to 15, wherein the affinity in decreased.

DETAILED DISCLOSURE

Surprisingly the present inventors have found that the sequences of the VH and VL can be mutated and the corresponding half-life does not necessarily correspond to the affinity of the binding domain. In particular modifications can be made to the VL where the affinity is maintained or decreased and the half-life is increased.

This allows the half-life to be designed and controlled for molecule to provide a half-life which is relevant to the therapeutic indication. In some embodiments long-half may be desirable. In some embodiments a moderate/medium half-life may be appropriate. In other embodiments a relatively short half-life may be appropriate.

A bespoke half-life as employed herein is a half-life which has been specifically designed for the binding domain by modifying the same.

A "binding domain or site" as employed herein is the part of the antibody that contacts the antigen. In one embodiment the binding domain contains at least one variable domain or a derivative thereof, for example a pair of variable domains or derivatives thereof, such as a cognate pair of variable domains or a derivative thereof.

In one embodiment the binding domain comprises 6 CDRs and a framework and together these elements contribute to the specificity of the binding interaction of the antibody or binding fragment.

Variable regions (also referred to herein as variable domains) generally comprise 3 CDRs and a suitable framework.

The term "antibody" as used herein refers to an immunoglobulin molecule capable of specific binding to a target antigen, such as a carbohydrate, polynucleotide, lipid, polypeptide, peptide etc., via at least one antigen recognition site (also referred to as a binding site herein), located in the variable region of the immunoglobulin molecule.

As used herein "antibody molecule" includes antibodies and binding fragments thereof. The term also extends to an antibody format comprising any one of the same.

Parent antibody as employed herein refers to the starting antibody before the mutations to change the half-life a made. The parent antibody may be humanised (which may include incorporate back-mutations containing so-called donor residues) or mutated, for example to remove lysine residues from a CDR or similar. However, modifications present in the parent antibody will not be for the purpose of changing/modifying the half-life. Parent antibody as employed herein includes antibody binding fragments.

"Antibody fragments" as employed herein refer to antibody binding fragments including but not limited to Fab, modified Fab, Fab', modified Fab', F(ab')2, Fv, single domain antibodies, scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216:165-181). Other antibody fragments for use in the present disclosure include the Fab and Fab' fragments described in International patent applications WO05/003169, WO05/003170 and WO05/003171. Multi-valent antibodies may comprise multiple specificities e.g. bispecific or may be monospecific (see for example WO92/22853, WO05/113605, WO2009/040562, WO2010/035012, WO2015/197772).

A "binding fragment" as employed herein refers to a fragment capable of binding a target peptide or antigen with sufficient affinity to characterise the fragment as specific for the peptide or antigen.

Specificity (or specific) as employed herein refers where the partners in the interaction only recognise each other or have significantly higher affinity for each other in comparison to non-partners, for example at least 2, 3, 4, 5, 6, 7, 8, 9, 10 times higher affinity, than for example a background level of binding.

Partners as employed herein refer to antigen and antibody binding or ligand and receptor type binding relationships.

At least one modification as employed herein, refers to substitution, addition or deletion of an amino acid, for example to change the properties of the sequence, for example the change hydrophobicity or similar.

The residues in antibody variable domains are conventionally numbered according to a system devised by Kabat et al., 1987. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M., J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The term "Fab fragment" as used herein refers to an antibody fragment comprising a light chain fragment comprising a VL (variable light) domain and a constant domain of a light chain (CL), and a VH (variable heavy) domain and a first constant domain (CH1) of a heavy chain.

A Fab' fragment as employed herein refers to a Fab fragment further comprising a hinge region.

The term "single-chain Fv" or abbreviated as "scFv", as used herein refers to an antibody fragment that comprises the VH and VL antibody domains linked (for example by a peptide linker) to form a single polypeptide chain. The constant regions of the heavy and light chain are omitted in this format. Single-chain Fv as employed herein includes disulfide stabilised versions thereof wherein in addition to the peptide linker a disulfide bond is present between the variable regions.

Disulfide stabilised scFv may eliminate the propensity of some variable region to dynamically breath, which relates to variable regions separating and coming together again.

The term "single domain antibody" as used herein refers to an antibody fragment consisting of a single monomeric variable antibody domain. Examples of single domain antibodies include $V_H$ or $V_L$ or $V_H H$.

The constant region domains, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example IgG4 molecules in which the serine at position 241 has been changed to proline as described in Angal et al., 1993, Molecular Immunology, 1993, 30:105-108 may be used. Accordingly, in the embodiment where the antibody is an IgG4 antibody, the antibody may include the mutation S241P.

In one embodiment the antibody binding fragment does not comprise an Fc region. "Does not comprise an Fc region" as employed herein refers to the lower constant domains, such as CH2, CH3 and CH4 are absent. However, constants domains such as CH1, CKappa/Clambda may be present.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

In one embodiment, the antibody heavy chain comprises a CH1 domain and the antibody light chain comprises a CL domain, either kappa or lambda.

In one embodiment, the antibody heavy chain comprises a CH1 domain, a CH2 domain and a CH3 domain and the antibody light chain comprises a CL domain, either kappa or lambda.

"Multispecific molecule" as employed herein refers to a molecule with the ability to specifically bind at least two distinct antigens, for example different antigens. In one embodiment the multispecific molecule is a bispecific, trispecific or tetraspecific molecule, in particular a bispecific molecule.

Examples of suitable multispecific molecules are known in the art.

In one embodiment multispecific formats include those known in the art and those described herein, such as wherein the molecule format is selected from the group comprising or consisting of: diabody, scdiabody, triabody, tribody, tetrabodies, tandem scFv, FabFv, Fab'Fv, FabdsFv, Fab-scFv, diFab, diFab', tandem scFv-Fc, scFv-Fc-scFv, scdiabody-Fc, scdiabody-CH3, Ig-scFv, scFv-Ig, V-Ig, Ig-V, Duobody and DVDIg, which are discussed in more detail below.

Molecule as employed herein is used in the biochemistry sense to refer to a group of atoms that form an organic, in particular proteinaceous mass, which includes a complex suitable for handling as a single entity under appropriate conditions once the complex has been formed.

Molecule and construct are used interchangeably herein, unless the context indicates otherwise. Although, construct may be employed more often to refer to a polynucleotide molecule and molecule may be employed more often to refer to an entity primarily comprising an amino acid sequence.

Antigens of interest, which may be targeted by an binding domain in the antibody molecule of the present disclosure, may also be any medically relevant protein such as those proteins upregulated during disease or infection, for example receptors and/or their corresponding ligands. Particular examples of cell surface proteins include: adhesion molecules, integrins such as β1 integrins (e.g. VLA-4), E-selectin, P selectin or L-selectin, CD2, CD3, CD4, CD5, CD7, CD8, CD11a, CD11b, CD18, CD19, CD20, CD23, CD25, CD33, CD38, CD40, CDW52, CD69, CD134 (OX40), ICOS, BCMP7, CD137, CD27L, CDCP1, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, and VEGF, and where appropriate, receptors thereof.

Soluble antigens include interleukins such as IL-1, IL-2, IL-3, IL-4, IL-5, IL-6, IL-8, IL-10, IL-12, IL-13, IL-15, IL-16 or IL-17, IL-21, IL-23, viral antigens for example respiratory syncytial virus or cytomegalovirus antigens, immunoglobulins, such as IgE, interferons such as interferon α, interferon β or interferon γ, tumour necrosis factor-α, tumor necrosis factor-β, colony stimulating factors such as G-CSF or GM-CSF, and platelet derived growth factors such as PDGF-α, and PDGF-β and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In the context of this specification "comprising" is to be interpreted as "including".

Aspects of the invention comprising certain elements are also intended to extend to alternative embodiments "consisting" or "consisting essentially" of the relevant elements.

Embodiments and descriptions of the disclosure may and will be combined where technically appropriate.

Any positive embodiment or combination thereof described herein may be the basis of a negative exclusion i.e. a disclaimer.

EXAMPLES

FIG. 1. Humanization and affinity reduction of antibody CA645. The heavy and light chain sequences of antibody CA645 (SEQ ID NO:1 and SEQ ID NO:6) are aligned with human germline acceptor framework sequences VH3 1-3 3-23/JH4 and Vκ1 2-1-(1) L5/Jκ4. Rabbit residues are in red, human residues are in black and CDRs are in blue (J-region CDR residues are shown but acceptor V-region CDRs are not). The grafted VH (gH) fSEQ ID NO:2 and SEQ ID NO:3) and VL (gL) (SEQ ID NO:7 and SEQ ID NO:8) sequences are shown below their corresponding human acceptor germline frameworks. Framework sequence differences between the rabbit and human framework sequences are shown with asterisks. Rabbit framework residues retained in the humanized grafts are highlighted in bold.

FIG. 2. Binding of FcRn to HSA and MSA in the presence or absence of CA645 gL4gH5 Fab. Binding to HSA in absence of Fab (red circle), binding to HSA in presence of Fab (red triangle), binding to MSA in absence of Fab (blue square), binding to MSA in presence of Fab (blue triangle).

FIG. 3. (A) Crystal structure of CA645 gL4gH5 Fab in complex with HSA (B) Superimposition of CA645 Fab-HSA with the crystal structure of FcRn-HSA complex, PDB code 4N0F. FcRn is composed of heavy chain, shown in green, and common β2-microglobulin (β2M), shown in orange (C) Superimposition of CA645 Fab-HSA with the crystal structures of HSA in complex with myristic acid, PDB code 1BJ5, shown in red, ibuprofen, PDB code 2BXG, shown in blue, and warfarin, PDB code 2BXD, shown in magenta. The seven fatty acid (FA) binding sites in albumin are also labelled.

Figure 4:
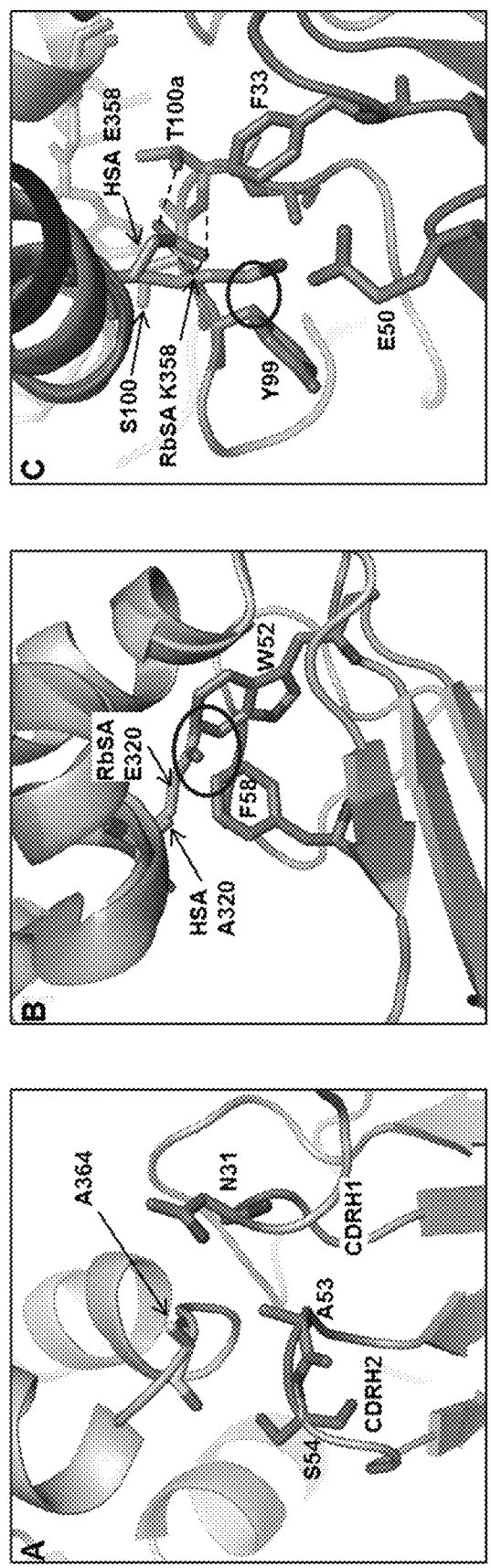

FIG. 4. Superimposition of CA645-HSA with RbSA. Close up views of regions around albumin residues at positions (A) 364, (B) 320 and (C) 358. CA645 heavy chain shown in blue; CA645 light chain shown in silver; HSA shown in wheat; RbSA shown in pink. Clashes are defined as two heavy atoms from different residues being within 2 Å of each other and are denoted by a black circle.

Figure 5:
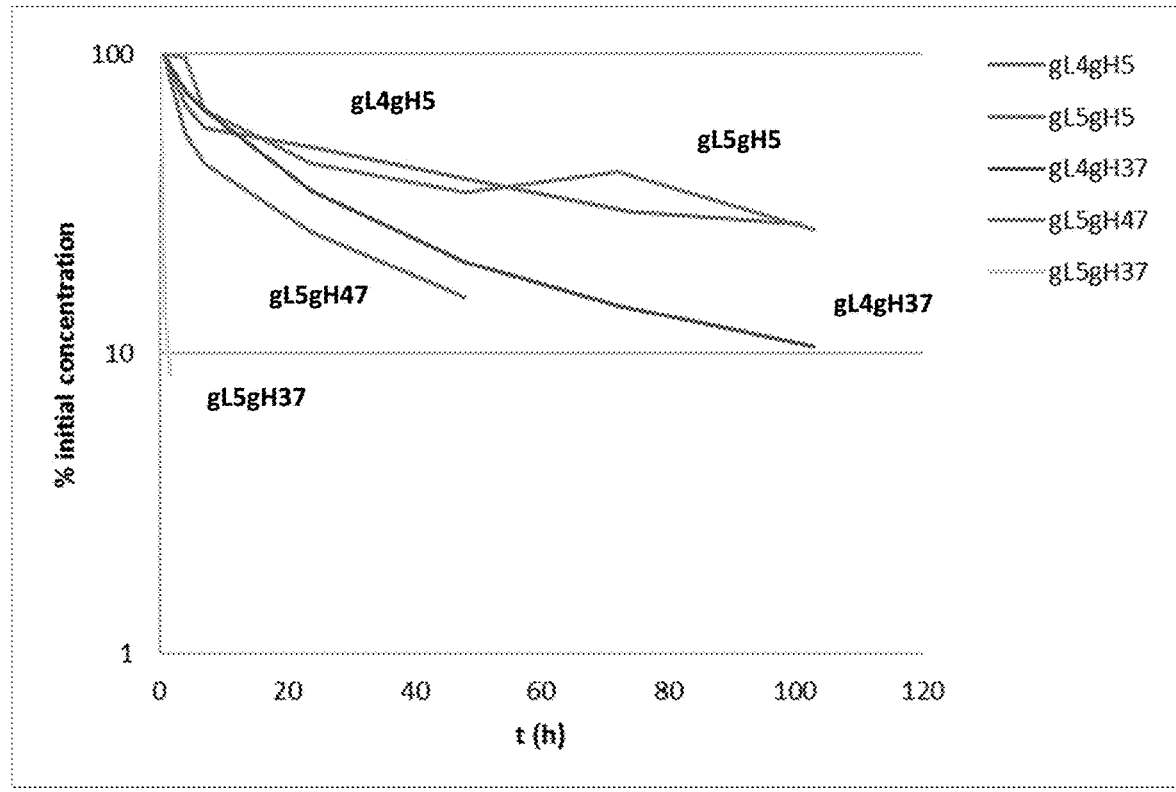

FIG. 5. Pharmacokinetics. CA645 Fab grafts were intravenously injected into mice at 10 mg/kg and serum concentrations of the Fabs were determined at various time points by ELISA. Data were normalized considering maximal concentration at the first time point.

Figure 6:
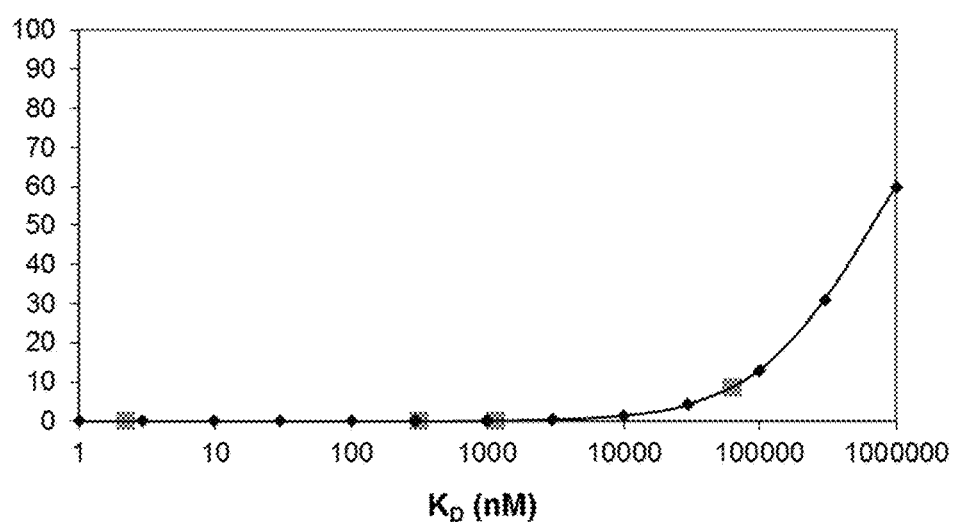

FIG. 6. Percentage of free CA645 Fab in blood versus affinity for MSA. % free Fab calculated for $K_D$ range of 1-10$^6$ nM (blue diamonds) using solution of mass action quadratic equation.[45] % free Fab for grafts gL4gH5, gL5gH5, gL4gH37 and gL5gH47 with affinities for MSA of 2.2, 316, 1146 and 62400 nM, respectively, are shown as red squares.

FIG. 7. Sequences of the disclosure

Table 1. Activity profiles of anti-human serum albumin (HSA) antibodies. Fluorescent microvolume assay technology (FMAT) screening of secreted anti-HSA antibodies in B cell supernatants for binding to 100 ng/ml HSA in the presence or absence of 25 µM albumin binding compounds (warfarin, ibuprofen, myristic acid, and copper chloride) and for binding to 100 ng/ml rat serum albumin (RSA). FL=fluorescence intensity. Equilibrium binding constants ($K_D$) of anti-HSA rabbit Fab fragments for human and mouse serum albumin (MSA), and of equivalent humanized IgG antibodies for HSA, MSA and RSA determined by surface plasmon resonance (SPR).

Table 2. Affinity of CA645 gL4gH5 Fab for serum albumin from different species. Association ($k_a$) and dissociation ($k_d$) rate constants and equilibrium binding constants ($K_D$) determined by SPR.

Table 3. X-ray data collection and refinement statistics. Values in parentheses are for highest-resolution shell.

Table 4. Binding kinetics and pharmacokinetics of CA645 Fab grafts. Association ($k_a$) and dissociation ($k_d$) rate constants and equilibrium binding constants ($K_D$) determined by SPR. 3 mice (M1-3)/group were dosed intravenously at 10 mg/kg with each CA645 graft. Mean and standard deviation (SD) of each group is shown. *measured by steady state.

Table 5 Shows affinity for various grafts.

Table 6. Affinity of CA645 gL4gH5 Fab for HSA over pH range 5.0-7.0.

Table 7. (A) (B) (C) Binding kinetics of CA645 Fab grafts. Association ($k_a$) and dissociation ($k_d$) rate constants and equilibrium binding constants ($K_D$) determined by SPR.

Antibody Discovery

Two Half Lop rabbits were immunised subcutaneously with 200 µg HSA (Jackson ImmunoResearch). Complete Freund's adjuvant (Sigma Aldrich) was co-administered with the first dose and subsequent doses included incomplete Freund's adjuvant. B cells were harvested from the rabbit sera and cultured for 7 days to induce clonal expansion and antibody secretion. Fluorescence microvolume assay technology (FMAT) was used to screen the supernatants for binding to HSA.[20-22] The supernatants were mixed with streptavidin beads (Bangs Laboratories, Inc) coated with biotinylated goat anti-rabbit Fc and Alexa Fluor 647 Chrompure Human Albumin (Jackson ImmunoResearch). Plates were read on an Applied Biosystems 8200 Cellular Detection System. The 48 wells with the highest fluorescence intensity (FL) signal were transferred to a single master plate and the screening repeated as before but with two additional screens. In one screen, Alexa Fluor 647 Chrompure Human Albumin was pre-incubated for 1 hour with a 25 µM solution of albumin binders; warfarin, ibuprofen, myristic acid, and copper chloride (all individually sourced from Sigma Aldrich). In the second screen, HSA was replaced with rat serum albumin (Sigma Aldrich) that had been labelled using Alexa Fluor 647® monoclonal antibody labelling kit (Molecular Probes).

Individual HSA specific B-cells were isolated by fluorescent foci method.[20-22] B cells from positive wells were mixed with streptavidin beads (Bangs Laboratories, Inc) coated with biotinylated-HSA (Jackson ImmunoResearch) and goat anti-rabbit Fc fragment fluorescein isothiocynate conjugate (Chemicon). Following 1 hour incubation at 37° C., antigen-specific B cells could be identified due to the presence of a fluorescent halo surrounding that B cell. An Olympus IX70 microscope and an Eppendorf micromanipulator were used to identify and transfer the individual B cells to PCR tubes. The heavy and light chain immunoglobulin variable (V) region genes of single cells were amplified by RT-PCR and cloned into UCB mammalian expression vectors containing rabbit heavy $C_H1$ and rabbit light Cκ regions, respectively. Following transient expression in HEK293 cells, anti-HSA recombinant Fabs were further screened in SPR binding assays against HSA and MSA.

Humanization

Albumin specific antibodies were humanized in silico by grafting the CDRs from antibody V-regions onto the Vκ1 and $V_H3$ human germline antibody V-region frameworks. The CDR's grafted from the donor to the acceptor sequence were as defined by Kabat et al.,[32] with the exception of CDR-H1 (residues 26-35) where the combined definitions of Kabat et al., and loop structure was used.[23] Where a framework residue differed between the donor rabbit sequence and the acceptor human sequence in a position that was considered to be important for retention of antigen binding, then the donor residue was included in the initial conservative graft.[21] The conservative graft genes were chemically synthesized by Entelechon, GmbH. Heavy chain graft genes (gH1) were cloned into two UCB expression vectors, one containing human γ1$C_H1$ domain and another containing the full human γ1 constant region. Light chain graft genes (gL1) were cloned into a UCB expression containing human kappa constant region (Km3 allotype). These constructs were subsequently modified by oligonucleotide-directed mutagenesis to create a number of different variants of both the heavy and light chain grafts. Heavy and light chain vectors were co-transfected into HEK293 cells and the recombinant Fab or IgG molecules screened using a SPR binding assay to measure affinity for HSA, MSA, RSA, CSA, RbSA and BSA.

Antibody Expression

Antibodies were transiently expressed in either HEK-293 cells using 293Fectin lipid transfection (Life Technologies, catalog #12347-019, according to the manufacturer's instructions) or CHO-S XE cells, a CHO-K1 derived cell line,[33] using electroporation. HEK-293 cells were used for small scale expression (<100 ml) to prepare antibodies for SPR analysis. CHO-S XE cells were used for large scale expression (1 litre) to prepare antibodies for crystallography and in vivo pharmacokinetic studies.

Protein Purification

Affinity chromatography was used to purify Fab protein from culture supernatants. Supernatants were passed over a HiTrap Protein G column (GE Healthcare) at a flow rate that gave a column contact time of 25 min. Following a washing step with PBS pH 7.4, the bound material was eluted with 0.1 M glycine pH 2.7 and neutralized with 2 m Tris-HCl (pH 8.5). Fractions containing Fab were pooled, quantified by absorbance at 280 nm, and concentrated using Amicon Ultra centrifugal filters (Merck Millipore). To isolate the monomeric fraction, size exclusion chromatography over a HiLoad 16/60, Superdex 200 column (GE Healthcare) equilibrated with PBS, pH 7.4, was used. Fractions containing monomeric Fab were pooled, quantified, concentrated and stored at 4° C.

Surface Plasmon Resonance

The binding affinities and kinetic parameters for the interactions of antibodies were determined by surface plasmon resonance (SPR) conducted on either a Biacore T200 or Biacore 3000 using CM5 sensor chips (GE Healthcare Bio-Sciences AB) and HBS-EP (10 mM HEPES, 150 mM NaCl, 3 mM EDTA, 0.05% v/v P20, pH7.4) running buffer. For analysis at pH 7.0, 6.0, 5.5 and 5.0, a running buffer of 40 mM citric acid, 80 mM sodium phosphate 50 mM NaCl, 3 mM EDTA, 0.05% v/v P20 was used. The required pH was achieved by altering the ratio of citric acid to sodium phosphate. All experiments were performed at 25° C. The antibody samples were captured to the sensor chip surface using either a human F(ab')$_2$-specific or human Fc-specific goat Fab (Jackson ImmunoResearch). Covalent immobilisation of the capture antibody was achieved by standard amine coupling chemistry to a level of 6000-7000 response units (RU).

Human (Jackson ImmunoResearch, catalog #009-000-051), mouse (Sigma Aldrich, catalog #A3559), rat (Sigma Aldrich, catalog #A6414), rabbit (Sigma Aldrich, catalog #A0764), bovine (Sigma Aldrich, catalog #05470) and cynomolgus (Equitech-Bio, #CMSA-0050) albumin were titrated over the captured antibody at various concentrations from 50 nM to 500 μM. Each assay cycle consisted of firstly capturing the antibody sample using a 1 min injection, before an association phase consisting of a 3 min injection of albumin, after which dissociation was monitored. After each cycle, the capture surface was regenerated with two 1 min injections of 40 mM HCl followed by 30 s of 5 mM NaOH. The flow rates used were 10 μl/min for capture, 30 μl/min for both the association and dissociation phases, and 10 μl/min for regeneration. A blank flow-cell was used for reference subtraction and buffer-blank injections were included to subtract instrument noise and drift. Kinetic parameters were determined by simultaneous global-fitting of the resulting sensorgrams to a standard 1:1 binding model using Biacore T200 Evaluation software v2.0.1 and BIAEvaluation software v4.1.1, with the exception of CA645 gL5gH47 which was fitted in prism using steady state affinity model.

To measure the effect of CA645 Fab on the binding potency of FcRn to albumin by SPR, a Biacore3000 instrument was used with a CM5 chip prepared by immobilisation of HSA and MSA on separate flow cells to levels of 270 RU and 247 RU respectively. FcRn samples were prepared over the range 50 nM to 50 μM in running buffer, (100 mM MES, 150 mM NaCl, 0.05% v/v P20, pH 5.5) and they also contained either zero or 100 nM CA645 Fab. Each assay cycle was run at a flow rate of 10 μl/min and consisted of either a 5 min injection of 100 nM CA645 Fab to pre-saturate immobilised albumin, followed by a 5 min injection of one of the above FcRn solutions prepared in the presence of CA645 Fab, or a 5 min injection of running buffer followed by a 5 min injection of one of the above FcRn solutions in the absence of CA645 Fab. In either case a third 5 min injection followed immediately at the end of the second injection, using the 'coinject' mode, comprising respectively, buffer or 100 nM CA645 Fab. A blank flow-cell was used for reference subtraction and blank cycles, where FcRn was replaced with buffer, were included to subtract drift and noise. Cycle regeneration was as above. Blank corrected plateau binding levels of FcRn were plotted in Prism and fitted to a steady state model.

Binding kinetics of wild type and mutant CA645 Fabs at pH 5.5 were also investigated in reverse format on the Biacore3000 using the immobilised albumin chip. In this case cycles were run where Fab solutions over the range 5 to 5000 nM were injected with 5 min association and dissociation phases. Buffer blank cycles were also included to correct for drift.

Crystallography

To prepare the complex, purified CA645 Fab and fatty acid-free HSA (Sigma Aldrich, catalog #A3782) were mixed in a molar ratio of 1:1 and incubated overnight at 4° C. Both CA645 Fab and the complex were purified by size exclusion chromatography over a HiLoad 16/60, Superdex 200 column (GE Healthcare) equilibrated with 50 mM NaCl, 25 mM Tris, 5% (v/v) glycerol. Fractions containing either CA645 Fab or the complex were pooled and concentrated to 10 mg/ml and 70 mg/ml, respectively. Conditions suitable for crystal growth were identified by the sitting drop vapour diffusion method using commercially available crystallization screens (Qiagen).

To generate diffraction quality crystals, hanging drop vapour diffusion method was used where 1 μl of protein solution was mixed with 1 μl of reservoir solution. For CA645 Fab, the reservoir contained 500 μl 2 M DL-Malic acid. Crystals were harvested and flash frozen in liquid nitrogen without additional cryoprotectant. Diffraction data to 2.68 Å was collected from a single crystal on the 104 beamline at Diamond Light Source, Oxford, UK and processed using MOSFLM and SCALA.[34-36] The structure of CA645 Fab was solved by molecular replacement with Phaser,[37] using coordinates of an in-house Fab structure as a search model. For the complex, the reservoir contained 500 μl 0.1 M Citric acid pH 4.4, 0.1 M di-Sodium hydrogen phosphate, 38% v/v Ethanol and 5% v/v Polyethylene glycol 1000 (PEG1000). The crystals were cryoprotected by multiple additions to the drop of 1 μl reservoir buffer containing 25% (v/v) PEG1000, until the concentration of PEG1000 in the drop reached 20%. To minimise crystal stress, each addition was spaced at least 1 hour apart. Crystals were harvested and flash frozen in liquid nitrogen. Diffraction data to 3.58 Å was collected from a single crystal on the 102 beamline at Diamond Light Source, Oxford, UK and processed using XDS.[38] The structure of the complex was solved by molecular replacement with Phaser using coordinates of CA645 Fab structure and HSA (PDB code 4G03)[39] as search models.

Both initial structures were refined with iterative cycles of simulated annealing, energy minimisation and manual rebuilding using CNS[40,41] and COOT.[42] Due to the rather low resolution of the complex, the model was constrained during refinement by using the DEN function of CNS. Model geometry was validated using Molprobity.[43] Molecular visualisations were generated with Pymol.[44] Data collection and refinement statistics are summarised in Table 3.

Accession Codes

Coordinates and structure factors of CA645 Fab and the CA645 Fab-HSA complex have been deposited in the Protein Data Bank (PDB) with accession codes, X and Y, respectively.

Mouse Pharmacokinetics

Three male BALB/c mice were dosed intravenously at 10 mg/kg with the antibody. Serial blood samples were collected from the tail venipuncture at several time points up to 100 hr post dose. To obtain sera, blood samples were centrifuged for 5 min at 10,000 rpm at room temperature and analysed for the antibody concentration by ELISA. An antibody against the Fab antigen and an anti-human kappa chain-Horseradish peroxidase conjugate (Stratech) was used as the capture and secondary antibody, respectively. A purified sample of the Fab antigen was used as the standard. Plates were developed using TMB peroxidase solution (Sigma-Aldrich) and read at 450 nm (reference at 630 nm). Pharmacokinetic parameters were calculated from the final dataset using Phoenix WinNonlin 6.2 software.

Calculation of Free CA645 Fab

To determine the concentration of unbound Fab (molecular weight=47907 Da), in 2 ml of blood, of a 20 g mouse, following a dose at 10 mg/kg the following equation was used:[31]

Free Fab concentration $x=(-b+\text{SQRT}(b^2-4ac))/2a$

Where:
$b=(-(K_A*[\text{Tab}])+1+(K_A*[\text{Tag}]))$
$a=K_A=1/K_D$
$c=(-[\text{Tab}])$
$K_D$=affinity of Fab
$K_A$=equilibrium constant of association
[Tab]=concentration of Fab (2087 nM)
[Tag]=concentration of albumin (600 μM)

To calculate percentage of free Fab % Free Fab= ([free Fab]/[Tab])*100

Results

Generation and Characterization of a mAb to Serum Albumin Across Species

To generate a panel of anti-HSA antibodies with cross species reactivity, two rabbits were immunized with HSA. B cells were harvested from the sera, cultured, stimulated to secrete IgG and screened using fluorescent microvolume assay technology (FMAT) to identify antigen-specific wells.[20-22] Further FMAT screens assessed binding to RSA and binding to HSA in the presence or absence of known albumin binding compounds; warfarin, ibuprofen, myristic acid, and copper chloride. Data for the five top-ranked antibodies is shown in Table 1. The fluorescence intensity signal for binding to HSA was lowest for CA645. However, CA645 did retain 80% of binding activity in the presence of the compounds whereas CA646, CA647, CA648 and CA649 retained only 40%. The levels of binding to HSA and RSA were most closely matched for CA645 and CA646, being within 5-fold. In contrast, the levels of binding to RSA by CA647, CA648 and CA649 were 9 to 18-fold lower than for HSA.

To recover the heavy and light chain variable regions of the five antibodies, fluorescent foci method was used to isolate single B cells and then RT-PCR was performed. The variable regions were cloned into expression vectors containing rabbit heavy $C_H1$ and light chain constant regions and then the DNA sequenced. This revealed that the antibody sequences were unique with the exception of CA645 and CA646 which had identical heavy chain sequences. Given CA645 and CA646 must bind to the same epitope through the heavy chain it is unclear why CA646 binding was more affected by the presence of ligands. Also determined from the sequencing was that the complementarity determining regions (CDRs) of all of the antibodies lacked histidine residues. This was important for further progression of these antibodies since histidine residues protonate at acidic pH and this can potentially disrupt antigen binding.

Following transfection of HEK293 cells, the recombinant Fab molecules were analysed by surface plasmon resonance (SPR) for affinity for HSA and mouse serum albumin (MSA). CA645 and CA646 both exhibited the strongest affinities for HSA, at 0.31 nM and 0.14 nM, respectively, and for MSA at 2.6 nM and 1.6 nM, respectively (Table 1). Furthermore, their affinities for HSA and MSA were the most closely matched of all of the antibodies. This was in line with the B cell supernatant screening data against HSA and RSA.

Humanization and Selection of Lead Candidate

All five antibodies were humanized by grafting the CDRs onto human Vκ1 and VH3 frameworks and back-mutating framework residues in positions considered important for retention of binding activity.[23] The humanization scheme for CA645 is shown in FIG. 1. Of note is that the framework three regions (residues 66-94) of the rabbit donor heavy chains were shorter than that of the human acceptor framework sequences. CA647 and CA649 were shorter by one residue whereas CA645 and CA646 (identical sequences) and CA648 were shorter by two residues. In all cases, the gap was retained in the initial conservative gL1gH1 graft.

The conservative grafts were expressed as human IgG1 antibodies and analysed by SPR for binding to HSA, MSA and RSA. The humanized IgGs displayed the same trend in binding to HSA and MSA as observed with the recombinant parental rabbit Fabs (Table 1). The affinities for HSA of CA647, CA648 and CA649 were similar to those of CA645 and CA646 but they showed a 6- to 10-fold reduction in affinity for MSA by comparison. The affinities for RSA of CA648 and CA649 also showed a 5- to 10-fold reduction in comparison with CA645 and CA646. CA646 exhibited marginally stronger affinities for HSA, MSA and RSA than CA645 but the transient expression yields were 4-fold lower at 35 mg/ml compared with 161 mg/ml (Table 1). Based on the near maximal retention of binding to HSA in the presence of known albumin binders, the consistent binding activity for albumin across multiple species and good yields in transient expression, CA645 was selected as our lead candidate for further progression. Further graft variants of CA645 gL IgH1 were generated by replacing rabbit donor residues with human acceptor residues and filling the gap in framework three of the heavy chain with the equivalent human residues. The graft variants were assessed on affinity for HSA and transient yield expression (data not shown). The final graft pairing selected was gL4 and gH5 (FIG. 1).

The affinities of CA645 gL4gH5 Fab for HSA, MSA, RSA and rabbit serum albumin (RbSA) were shown to be 4.6, 7.1, 54 and 162 nM, respectively (Table 2). Significantly for utility of CA645 gL4gH5 Fab in cynomolgus monkey toxicology studies and disease models, the affinity for cynomolgus serum albumin (CSA) was very similar to that of HSA at 3.3 nM. In addition, CA645 Fab failed to bind to bovine serum albumin.

To determine whether CA645 gL4gH5 Fab is likely to remain bound to albumin in the acidic environment of the early endosome and be recycled to the cell surface, the affinity was measured at pH 5.0-7.0 (Table S1). The affinities of CA645 gL4gH5 Fab for HSA at pH 5.0, pH 5.5, pH 6.0, and pH 7.0 were 7.1, 10.7, 12.5 and 13.3 nM indicating that binding is largely unaffected within this physiologically relevant pH range.

To determine whether HSA can bind to FcRn in the presence of CA645 gL4gH5 Fab, SPR was used. The kinetic assays were conducted at pH5.5 to ensure optimal binding by FcRn to albumin. HSA or MSA was bound directly onto the sensor chip, then either CA645 gL4gH5 Fab, to saturate CA645 albumin binding sites, or running buffer was injected into the flow cell. This was followed by an injection of FcRn plus CA645 Fab, or FcRn alone. CA645 Fab was included in the co-injection with FcRn to maintain CA645 binding site saturation. FIG. 2 shows the levels of FcRn binding to both HSA and MSA following subtraction of the signals for CA645. Binding by FcRn to both albumins was unaffected by the presence of CA645 gL4gH5 Fab.

Crystallography

To identify where CA645 binds to HSA, the crystal structure of CA645 Fab-HSA complex was determined. The CA645 Fab-HSA complex protein preparation was concentrated to 70 mg/ml,[24] and crystallized using ethanol and PEG1000 as precipitants. To aid solving the structure of the complex with molecular replacement, we also determined the structure of unbound CA645 Fab. We observed single copies of both the Fab and Fab-HSA complex in the asymmetric units of their respective crystals (Table 3). The structure of free Fab was refined to 2.68 Å with a final $R_{work}$ value of 21.14% and $R_{free}$ value of 25.13%. The structure of the complex was refined to 3.6 Å with a final $R_{work}$ value of 21.38% and $R_{free}$ value of 25.23%.

The crystal structure of the CA645 Fab-HSA complex showed that CA645 binds to domain II of HSA (FIG. 3A). Superimposition of the crystal structure of FcRn in complex with HSA (PDB code 4N0F),[25] showed that CA645 does not block binding of HSA to FcRn (FIG. 3B). HSA contains seven fatty acid (FA) binding sites. Sites FA7 and FA3/FA4 are the two main drug binding sites.[26] Drugs also bind at sites FA1, FA5 and FA6 but with weaker affinity. Metal ion binding sites are located between domains I and II and at a site at the N-terminus.[27] Superimposition of the complex with the crystal structures of HSA in complex with warfarin (PDB code 2BXD),[28] ibuprofen (PDB code 2BXG)[28] and myristic acid (PDB code 1BJ5)[29] showed that CA645 binds close to site FA6 and does not occlude the main drug (FA7 and FA3/FA4), fatty acid or metal ion binding sites (FIG. 3C).

The binding kinetics of CA645 gL4gH5 Fab to HSA in comparison with those for MSA, CSA, RSA and RbSA (Table.2) may be explained by close visual inspection of the crystal structure. The epitope on HSA is formed by residues F206, G207, R209, C316, K317, AEAKD 320-324, K351, E354, E358, K359, C361, A362 and A364. The affinities of CA645 for CSA (3.3 nM) and MSA (7.1 nM) are very similar to the affinity for HSA (4.6 nM). This is likely due to the presence in CSA and MSA of the same residues that form the epitope in HSA. RSA shares all of these residues except for position 364 which is glycine. Position 364 is located at the tip of a short loop (positions 362-365) that links two α-helices (positions 366-398 and 342-361) together (FIG. 4A). This short loop is bound by CDR's 1 and 2 of the CA645 heavy chain. The affinity of CA645 for RSA is approximately 10-fold lower than for HSA. It is possible that the absence of the alanine side chain increases the flexibility of the loop, compared with that of HSA, and alters the binding kinetics.

RbSA shares all of the HSA epitope residues except positions 320, 358 and 364. Superimposition of the crystal structure of RbSA (PDB code 3V09)[30] showed clear clashes with CA645 Fab at positions 320 and 358, and a potential clash at position 364. In RbSA, position 364 is aspartic acid and whilst there was no clear clash, this position is a contact residue and therefore likely to influence binding by CA645. In HSA, position 320 is alanine and it forms a hydrophobic interaction with F58 of CDRH2 (FIG. 4B). In RbSA, position 320 is glutamic acid and it clashes with CDRH2 residues W52 and F58. Residue E358 in HSA forms a hydrogen bond network with S100 and T100a of CDRH3 (FIG. 4C). Position 358 in RbSA is lysine and it clashes with Y99 of CDRH3. The weaker affinity of CA645 for RbSA compared with HSA is entirely due to an 18-fold reduction in the association rate (Table.2). This is likely to be caused by the presence in RbSA of the larger side chains at positions 320 and 358, and possibly 364.

Pharmacokinetics of Reduced Affinity Variants

To investigate the correlation between the half-life of CA645 and its affinity for albumin, we generated a panel of mutants of CA645 gL4gH5 Fab with a broad range of reduced affinities and then analysed their pharmacokinetic properties in mice. The mutations were designed using the crystal structure of the CA645 gL4gH5 Fab-HSA complex as a guide. Oligonucleotide-directed mutagenesis was used to generate twenty variants across six residue positions of the heavy chain and twenty seven variants across six residue positions of the light chain (Tables 4, S2A, S2B and S2C). BALB/c mice were dosed by a single intravenous injection at 10 mg/kg with CA645 gL4gH5 Fab and a subset of four of the Fab variants, gL5gH5, gL4gH37, gL5gH37 and gL5gH47. Blood sera were sampled over 103 hours and the level of Fab quantified by ELISA.

CA645 gL5gH37 showed no detectable binding to HSA by SPR and was cleared rapidly with a serum half-life of only 0.48±0.06 h (Table 4). This is in line with the short half-life (0.7 h) of an anti-TNF Fab observed in rats.[19] In contrast gL4gH5 exhibited a significantly extended half-life of 84±4.6 h. The variant with the weakest affinity for which there was no difference in pharmacokinetic profile from gL4gH5 was gL5gH5 (FIG. 5). gL5gH5 contained a single mutation in the light chain, W30A, and its affinity was 453 nM. This affinity was 368-fold weaker than that of gL4gH5 (1.23 nM) but its half-life (96.7±20.4 h) was equivalent to that of gL4gH5. A change in the pharmacokinetic profile was observed for gL4gH37. It has a single mutation in the heavy chain, F58E, and its affinity was 955 nM. This affinity was 776-fold lower than gL4gH5 but the half-life still extended to 61±16.8 h. gL5gH47 contained one mutation in the light chain, W30A, and one mutation in the heavy chain, T100aS, and had an affinity of 52 μM, as measured by steady state SPR. This affinity was 42,276-fold weaker than that of gL4gH5, and yet the pharmacokinetic profile did not differ dramatically from gL4gH37 and the half-life increased to 26.3±3.1 h.

The mutants were designed and selected on the basis of affinity for HSA but the pharmacokinetic model was murine. Therefore, to confirm that the affinities of the mutants for HSA reflected their affinities for albumin in a mouse, SPR was repeated (Table.5). The affinities of gL4gH5 and gL5gH5 were 1.8 and 254 nM for HSA, and similarly 2.2 and 316 nM for MSA. These data were in line with the previously determined affinities of gL4gH5 and gL5gH5 for HSA of 1.23 and 453 nM, respectively.

Using a solution of the mass action quadratic equation, we can estimate the percentage of free Fab in the blood for each of the variants.[31] If we assume the concentration of MSA (65.9 kDa) is 44 g/L and the volume of the blood of a 20 g mouse is 2 ml, then for a dose at 10 mg/kg, the concentration of CA645 Fab (47.9 kDa) will be 2087 nM. FIG. 6 shows a graph of the percentage of free Fab versus affinity for albumin in the range 1-$10^6$ nM. With an affinity for MSA of 2.2 nM, just 0.0003% of gL4gH5 Fab is predicted to be unbound in blood. The affinity for MSA of gL5gH5 Fab is 316 nM. It has a pharmacokinetic profile and half-life that matches that of gL4gH5, and is calculated to have a similarly low level of free Fab at 0.05%. We were unable to measure the affinities of gL4gH37 and gL5gH47 Fabs for MSA. However, as the affinities of gL4gH5 and gL5gH5 were both 1.2-fold weaker for MSA than for HSA (Table 5), it is reasonable to predict that the affinities of gL4gH37 and gL5gH47 will be proportionately 1.2-fold weaker. Therefore, with predicted affinities for MSA of 1146 nM and 62.4 μM, it is calculated that 0.17% of gL4gH37 and 8.57% of gL5gH47, respectively, are potentially free in blood.

TABLE 1

Binding of various antibodies generated

| | FMAT | | | SPR | | | | | |
|---|---|---|---|---|---|---|---|---|---|
| | B cell sup | | | Rabbit Fab | | Humanized IgG | | | |
| mAb CA no. | HSA (FL) | HSA + compounds (FL) | RSA (FL) | HSA $K_D \times 10^{-9}$ (M) | MSA $K_D \times 10^{-9}$ (M) | HSA $K_D \times 10^{-9}$ (M) | MSA $K_D \times 10^{-9}$ (M) | RSA $K_D \times 10^{-9}$ (M) | Yield (mg/ml) |
| 645 | 272 | 220 | 114 | 0.31 | 2.6 | 0.82 | 2.9 | 7.9 | 161 |
| 646 | 2310 | 964 | 484 | 0.14 | 1.6 | 0.57 | 1.7 | 4.5 | 35 |
| 647 | 1213 | 520 | 69 | 0.60 | 36.0 | 1.30 | 26 | 10 | 23 |
| 648 | 1048 | 465 | 72 | 0.33 | 12.0 | 0.13 | 23 | 54 | 312 |
| 649 | 1338 | 534 | 142 | 0.54 | 13.0 | 0.32 | 17 | 44 | 188 |

TABLE 2

Binding Kinetics of CA645 gL4Gh5 Fab to HAS, MSA, CSA, RSA and RbSA

| Albumin | $k_a \times 10^4$ (1/Ms) | $k_d \times 10^{-4}$ (1/s) | $K_D \times 10^{-9}$ (M) |
|---|---|---|---|
| Human | 9.0 | 4.1 | 4.6 |
| Mouse | 4.8 | 3.4 | 7.1 |
| Rat | 2.4 | 13 | 54 |
| Cynomolgus | 10 | 3.5 | 3.3 |
| Rabbit | 0.2 | 2.9 | 162 |
| Bovine | — | — | No binding |

TABLE 3

X-ray data

| | Fab_645 | Fab_645-HSA |
|---|---|---|
| Data collection | | |
| Space group | P 3₁ 2 1 | P 3₁ 2 1 |
| Cell dimensions | | |
| a, b, c (Å) | 111.21, 111.21, 89.20 | 217.68, 217.68, 78.68 |
| α, β, γ (°) | 90.00, 90.00, 120.00 | 90.00, 90.00, 120.00 |
| Resolution (Å) | 30.0-2.68 (2.82-2.32) * | 30.0-3.58 (3.79-3.58) * |
| $R_{merge}$ | 0.117 (0.357) | 0.157 (0.612) |
| $R_{meas}$ | 0.120 (0.365) | 0.108 (0.439) |
| $CC_{1/2}$ | 99.7 (98.2) | 99.5 (78.5) |
| I/σI | 23.0 (10.1) | 7.57 (1.64) |
| Completeness (%) | 99.5 (99.4) | 93.9 (86.1) |
| Redundancy | 21.5 (22.2) | 2.4 (1.9) |
| Refinement | | |
| Resolution (Å) | 30.00-2.68 | 30.00-3.6 |
| No. reflections | 389, 935 | 110, 160 |
| $R_{work}/R_{free}$ | 0.2114/0.2513 | 0.2138/0.2523 |
| No. atoms | | |
| Protein | 3311 (excluding H) | 7870 (ex H) |
| Water | 37 | — |
| B-factors | | |
| Protein | 31.55 | 115.14 |
| Water | 24.24 | — |
| R.m.s. deviations | | |
| Bond lengths (Å) | 0.007 | 0.010 |
| Bond angles (°) | 1.447 | 1.446 |

TABLE 4

| CA645 Grafts | mutation Light chain | mutation Heavy chain | SPR $k_a \times 10^5$ (1/Ms) | SPR $k_d \times 10^{-4}$ (1/s) | SPR $K_D \times 10^{-9}$ (M) | Half-life (h) M1 | Half-life (h) M2 | Half-life (h) M3 | Half-life (h) Mean | Half-life (h) SD |
|---|---|---|---|---|---|---|---|---|---|---|
| gL4gH5 | — | — | 1.39 | 1.72 | 1.23 | 85 | 88 | 79 | 84 | 4.6 |
| gL5gH5 | W30A | — | 1.26 | 571 | 453 | 120 | 82 | 88 | 96.7 | 20.4 |
| gL4gH37 | — | F58E | 0.61 | 583 | 955 | 55 | 48 | 80 | 61 | 16.8 |
| gL5gH47 | W30A | T100aS | — | — | 52 μM* | 27 | 23 | 29 | 26.3 | 3.1 |
| gL5gH37 | W30A | F58E | — | — | NB | 0.54 | 0.42 | 0.47 | 0.48 | 0.06 |

TABLE 5

| CA645 Grafts | Albumin species | $k_a \times 10^4$ (1/Ms) | $k_d \times 10^{-4}$ (1/s) | $K_D \times 10^{-9}$ (M) |
|---|---|---|---|---|
| gL4gH5 | HSA | 22 | 4.0 | 1.8 |
| gL4gH5 | MSA | 31 | 6.8 | 2.2 |
| gL5gH5 | HSA | 8.5 | 220 | 254 |
| gL5gH5 | MSA | 1.2 | 38 | 316 |

TABLE 6

| pH | KD (nM) |
|---|---|
| 5.0 | 7.1 |
| 5.5 | 10.7 |
| 6.0 | 12.5 |
| 7.0 | 13.3 |

TABLE 7A

| CA645 Grafts | Light chain mutation | Heavy chain mutation | $k_a \times 10^4$ (1/Ms) | $k_d \times 10^{-4}$ (1/s) | $K_D \times 10^{-9}$ (M) |
|---|---|---|---|---|---|
| gL4gH5 | — | — | 5.75 | 1.23 | 2.14 |
| gL10gH5 | S28A | — | 13.80 | 1.72 | 1.03 |
| gL12gH5 | S28D | — | 5.54 | 1.04 | 1.88 |
| gL13gH5 | S28I | — | 5.76 | 1.08 | 1.88 |
| gL14gH5 | S28L | — | 5.77 | 0.87 | 1.51 |
| gL27gH5 | F32Y | — | 6.21 | 5.86 | 9.44 |
| gL34gH5 | S93T | — | 5.58 | 1.90 | 3.41 |
| gL35gH5 | S93V | — | 5.21 | 2.90 | 5.57 |
| gL4gH43 | — | G98E | 5.29 | 3.91 | 7.39 |
| gL4gH44 | — | G98L | 5.35 | 2.26 | 4.22 |
| gL4gH45 | — | G98V | 5.38 | 4.44 | 8.25 |
| gL4gH27 | — | A53G | 4.83 | 0.84 | 1.73 |
| gL4gH28 | — | A53V | 4.85 | 5.15 | 10.62 |
| gL4gH29 | — | A53S | 4.77 | 3.80 | 7.97 |
| gL4gH30 | — | A53T | 4.38 | 10.2 | 23.17 |
| gL4gH38 | — | F58Y | 4.75 | 5.81 | 12.23 |
| gL4gH39 | — | G98I | 5.35 | 7.50 | 14.01 |
| gL4gH40 | — | G98T | 5.56 | 3.56 | 6.40 |
| gL4gH41 | — | G98D | 5.37 | 3.51 | 6.54 |
| gL4gH42 | — | G98Q | 5.31 | 2.22 | 4.17 |
| gL4gH5 | — | — | 5.60 | 1.40 | 2.51 |

TABLE 7B

| CA645 Grafts | Light chain mutation | Heavy chain mutation | $k_a \times 10^4$ (1/Ms) | $k_d \times 10^{-4}$ (1/s) | $K_D \times 10^{-9}$ (M) |
|---|---|---|---|---|---|
| gL4gH5 | — | — | 5.91 | 1.61 | 2.72 |
| gL15gH5 | S31R | — | 6.01 | 2.77 | 4.62 |
| gL16gH5 | S31W | — | 5.53 | 1.69 | 3.06 |
| gL17gH5 | S31N | — | 5.88 | 3.23 | 5.50 |
| gL18gH5 | S31I | — | 5.32 | 8.23 | 15.47 |
| gL19gH5 | S31D | — | 5.20 | 2.60 | 5.00 |
| gL20gH5 | S31Q | — | 5.55 | 7.94 | 14.30 |
| gL21gH5 | S31E | — | 5.10 | 3.23 | 6.34 |
| gL22gH5 | S31H | — | 5.57 | 4.78 | 8.58 |
| gL23gH5 | S31L | — | 5.49 | 8.14 | 14.82 |
| gL24gH5 | S31V | — | 5.47 | 8.83 | 16.14 |
| gL25gH5 | S31F | — | 5.62 | 2.17 | 3.85 |
| gL26gH5 | S31Y | — | 6.01 | 2.48 | 4.13 |
| gL4gH31 | — | S54V | 4.00 | 1.67 | 4.18 |
| gL4gH32 | — | S54I | 3.86 | 1.69 | 4.38 |
| gL4gH33 | — | S54L | 3.89 | 2.40 | 6.18 |
| gL4gH34 | — | S54Q | 3.85 | 4.22 | 10.97 |
| gL4gH35 | — | S54E | 2.65 | 3.99 | 15.06 |
| gL4gH5 | — | — | 5.86 | 1.58 | 2.70 |

TABLE 7C

| CA645 Grafts | Light chain mutation | Heavy chain mutation | $k_a \times 10^4$ (1/Ms) | $k_d \times 10^{-4}$ (1/s) | $K_D \times 10^{-9}$ (M) |
|---|---|---|---|---|---|
| gL4gH5 | — | — | 5.62 | 1.67 | 2.97 |
| gL11gH5 | S28N | — | 5.64 | 2.49 | 4.42 |
| gL28gH5 | S67L | — | 5.90 | 1.09 | 1.85 |
| gL29gH5 | S67V | — | 5.77 | 1.03 | 1.78 |
| gL30gH5 | S67I | — | 5.84 | 0.94 | 1.61 |
| gL31gH5 | S67T | — | 5.72 | 1.42 | 2.49 |
| gL32gH5 | S67Q | — | 5.86 | 1.43 | 2.44 |
| gL33gH5 | S67E | — | 5.40 | 1.79 | 3.32 |
| gL4gH46 | — | V96Y | 5.64 | 1.84 | 3.26 |
| gL4gH47 | — | T100aS | 6.16 | 34.10 | 55.39 |
| gL4gH5 | — | — | 5.57 | 2.11 | 3.80 |

REFERENCES

1. Kontermann R E. Strategies for extended serum half-life of protein therapeutics. Curr Opin Biotechnol 2011; 22: 868-876.
2. Sleep D, Cameron J, Evans L R. Albumin as a versatile platform for drug half-life extension. Biochim Biophys Acta 2013; 1830: 5526-5534.
3. Peters T Jr. All About Albumin: Biochemistry, Genetics, and Medical Applications 1996; San Diego, Calif.: Academic Press.
4. Chaudhury C, Mehnaz S, Robinson J M, Hayton W L, Pearl D K, Roopenian D C, Anderson C L. The major histocompatibility complex-related Fc receptor for IgG (FcRn) binds albumin and prolongs its lifespan. J Exp Med 2003; 197: 315-322.
5. Junghans R P, Anderson C L. The protection receptor for IgG catabolism is the beta2-microglobulin-containing neonatal intestinal receptor. Proc Natl Acad Sci USA 1996; 93: 5512-5516.
6. Müller D, Karle A, Meissburger B, Höfig I, Stork R, Kontermann R E. Improved pharmacokinetics of recombinant bispecific antibody molecules by fusion to human serum albumin. J Biol Chem 2007; 282: 12650-12660.
7. Elsadek B, Kratz F. Impact of albumin on drug delivery—New applications on the horizon. J Control Release 2012; 157: 4-28.
8. Sorensen A R, Stidsen C E, Ribel U, Nishimura E, Stuns J, Jonassen I, Bouman S D, Kurtzhals P, Brand C L. Insulin detemir is a fully efficacious, low affinity agonist at the insulin receptor. Diabetes Obes Metab 2010; 12: 655-673.
9. Trüssel S, Dumelin C, Frey K, Villa A, Buller F, Neri D. New strategy for the extension of the serum half-life of antibody fragments. Bioconjug Chem 2009; 20: 2286-2292.
10. Dennis M S, Zhang M, Meng Y G, Kadkhodayan M, Kirchhofer D, Combs D, Damico L A. Albumin binding as a general strategy for improving the pharmacokinetics of proteins. J Biol Chem 2002; 277: 35035-35043.
11. Nguyen A, Reyes A E 2nd, Zhang M, McDonald P, Wong W L, Damico L A, Dennis M S. The pharmacokinetics of an albumin-binding Fab (AB.Fab) can be modulated as a function of affinity for albumin. Protein Eng Des Sel 2006; 9: 291-297.
12. Hopp J, Hornig N, Zettlitz K A, Schwarz A, Fuss N, Müller D, Kontermann R E. The effects of affinity and valency of an albumin-binding domain (ABD) on the half-life of a single-chain diabody-ABD fusion protein. Protein Eng Des Sel 2010; 23: 827-834.
13. Andersen J T, Pehrson R, Tolmachev V, Daba, M B, Abrahmsén L, Ekblad C. Extending half-life by indirect targeting of the neonatal Fc receptor (FcRn) using a minimal albumin binding domain. J Biol Chem 2011; 286: 5234-5241.
14. Tijink B M, Laeremans T, Budde M, Stigter-van Walsum M, Dreier T, de Haard H J, Leemans C R, van Dongen G A Improved tumor targeting of anti-epidermal growth factor receptor Nanobodies through albumin binding: taking advantage of modular Nanobody technology. Mol Cancer Ther 2008; 8: 2288-2297.
15. Van Roy M, Ververken C, Beirnaert E, Hoefman S, Kolkman J, Vierboom M, Breedveld E, Hart B, Poelmans S, Bontinck L, Hemeryck A, Jacobs S, Baumeister J, Ulrichts H. The preclinical pharmacology of the high affinity anti-IL-6R Nanobody® ALX-0061 supports its clinical development in rheumatoid arthritis. Arthritis Research & Therapy 2015.
16. Holt L J, Basran A, Jones K, Chorlton J, Jespers L S, Brewis N D, Tomlinson I M. Anti-serum albumin domain antibodies for extending the half-lives of short lived drugs. Protein Eng Des Sel 2008; 21: 283-288.
17. O'Connor-Semmes R L, Lin J, Hodge R J, Andrews S, Chism J, Choudhury A. Nunez D J. GSK2374697, a novel albumin-binding domain antibody (AlbudAb), extends systemic exposure of exendin-4: first study in humans-PK/PD and safety. Clin Pharmacol Ther 2014; 96: 704-712.
18. Flanagan R J, Jones A L. Fab antibody fragments. Drug Safety 2004; 27: 1115-1133.
19. Smith B J, Popplewell A, Athwal, D, Chapman A P, Heywood S, West S M, Carrington B, Nesbitt A, Lawson A D, Antoniw P, Eddelston A, Suitters A. Prolonged in vivo residence times of antibody fragments associated with albumin. Bioconjug Chem 2001; 12: 750-756.
20. Lightwood D J, Carrington B, Henry A J, McKnight, A J, Crook K, Cromie K, Lawson A D. Antibody generation through B cell panning on antigen followed by in situ culture and direct RT-PCR on cells harvested en masse from antigen-positive wells. J Immunol Methods 2006; 316: 133-143.
21. Tickle S, Adams R, Brown D, Griffiths M, Lightwood D J, Lawson A D. High-throughput screening for high affinity antibodies. J Lab Auto 2009; 14(5): 303-307.

22. Clargo A M, Hudson A R, Ndlovu W, Wootton R J, Cremin L A, O'Dowd V L, Nowosad C R, Starkie D O, Shaw S P, Compson J E, White D P, MacKenzie B, Snowden J R, Newnham L E, Wright M, Stephens P E, Griffiths M R, Lawson A D, Lightwood D J. The rapid generation of recombinant functional monoclonal antibodies from individual, antigen-specific bone marrow-derived plasma cells isolated using a novel fluorescence-based method. MAbs 2014; 6: 143-159.
23. Adair J R, Athwal D S, Emtage J S. Humanised Antibodies International Patent Publication. 1991; WO91/09967.
24. Curry S. Lessons from the crystallographic analysis of molecule binding to Human Serum Albumin. Drug Metab Pharmacokinet 2009; 24(4): 342-357.
25. Oganesyan V, Damschroder M M, Cook, K E, Li, Q, Gao C, Wu H, Dall'acqua W F. Structural insights into neonatal Fc receptor-based recycling mechanisms. J Biol Chem 2014; 289: 7812-7824.
26. Ascenzi, P. & Fasano, M. Allostery in a monomeric protein: The case of human serum albumin. Biophys Chem 2010; 148: 16-22.
27. Bal W, Sokolowska M, Kurowska E, Faller P. Binding of transition metal ions to albumin: Sites, affinities and rates. Biochim Et Biophys Act 2013; 1830 (12): 5444-5445.
28. Ghuman J, Zunszain P A, Petitpas I, Bhattacharya A A, Otagiri M, Curry S. Structural basis of the drug-binding specificity of human serum albumin. J Mol Biol 2005; 353: 38-52.
29. Curry S, Mandelkow H, Brick P, Franks N. Crystal structure of human serum albumin complexed with fatty acid reveals an asymmetric distribution of binding sites. Nat Struct Biol 1998; 5: 827-835
30. Majorek K A, Porebski P J, Dayal A, Zimmerman M D, Jablonska K, Stewart A J, Chruszcz M, Minor W. Structural and immunologic characterization of bovine, horse, and rabbit serum albumins. Mol Immunol 2012; 52: 174-182
31. Steward M W, Steensgard J. Antibody affinity: thermodynamic aspects and biological significance 1983. CRC Press. 32. Kabat E A, Wu T T, Perry H M, Gottesman K S, Foeller C. Sequences of proteins of immunological interest, 1991; 5th edit Public Health Service, National Institutes of Health, Bethesda, Md.
33. Cain K, Peters S, Hailu H, Sweeney B, Stephens P, Heads J, Sarkar K, Ventom A, Page C, Dickson A. A CHO cell line engineered to express XBP1 and ERO1-Lα has increased levels of transient protein expression. Biotechnol Prog 2013; 29: 697-706.
34. Leslie A G W. Acta Cryst 2006; D62: 48-57
35. Leslie A G W, Powell H R. Evolving Methods for Macromolecular Crystallography 2007; 245: 41-51; ISBN 978-1-4020-6314-5
36. Evans P. Acta Cryst 2006; D62: 72-82
37. McCoy A J, Grosse-Kunstleve R W, Adams P D, Winn M D, Storoni L C, Read R J. Phaser crystallographic software. J Appl Cryst 2007; 40: 658-674
38. Kabsch W. XDS. Acta Cryst 2010; D66: 125-132.
39. Cao H. L, Yin D C. High-resolution Crystal Structural Variance Analysis between Recombinant and Wild-type Human Serum Albumin. To be published. DOI:10.2210/pdb4g03/pdb
40. Brünger A T, Adams P D, Clore G M, DeLano W L, Gros P, Grosse-Kunstleve R W, Jiang J S, Kuszewski J, Nilges M, Pannu N S, Read R J, Rice L M, Simonson T, Warren G L. Crystallography & NMR system: A new software suite for macromolecular structure determination. Acta Crystallogr D Biol Crystallogr 1998; 54 (Pt 5): 905-21
41. Brünger A T. Version 1.2 of the Crystallography and NMR system. Nature Protocols 2007; 2: 2728-2733
42. Emsley P, Cowtan K. Coot: model-building tools for molecular graphics. Acta Crystallogr D Biol Crystallogr 2004; D60: 2126-32
43. Chen V B, Arendall III W B, Headd J J, Keedy D A, Immormino R M, Kapral G J, Murray L W, Richardson J S, Richardson D C. Acta Crystallogr D Biol Crystallogr 2010; D66: 12-21
44. DeLano W L The PyMOL Molecular Graphics System 2002; DeLano Scientific LLC, San Carlos, Calif.

The invention claimed is:

1. A binding domain comprising a variable heavy (VH) domain and variable light (VL) domain specific to a serum carrier protein, wherein the VH and VL sequences are selected from combinations of SEQ ID NOs: 3 and 9, SEQ ID NOs: 4 and 8, SEQ ID NOs: 4 and 9, and SEQ ID NOs: 5 and 9.

2. The binding domain according to claim 1, wherein the serum carrier protein is human serum albumin.

3. The binding domain according to claim 2, wherein the binding domain binds to domain II of human serum albumin.

4. The binding domain according to claim 1, wherein the VL and VH sequences are SEQ ID NO: 9 and SEQ ID NO: 3, respectively.

5. The binding domain according to claim 1, wherein the VL and VH sequences are SEQ ID NO: 8 and SEQ ID NO: 4 respectively.

6. The binding domain according to claim 1, wherein the VL and VH sequences are SEQ ID NO: 9 and SEQ ID NO: 5 respectively.

7. The binding domain according to claim 1, wherein the VL and VH sequences are SEQ ID NO: 9 and SEQ ID NO: 4 respectively.

8. The binding domain according to claim 1, wherein the binding domain is humanized.

9. The binding domain according to claim 8, wherein the humanized binding domain comprises a human IgG framework in the VH and/or VL.

10. A pharmaceutical composition comprising the binding domain according to claim 1.

11. An antibody molecule comprising the binding domain according to claim 1.

12. A pharmaceutical composition comprising the antibody molecule according to claim 11.

* * * * *

SEQUENCE LISTING

```
<160> NUMBER OF SEQ ID NOS: 9

<210> SEQ ID NO 1
<211> LENGTH: 118
<212> TYPE: PRT
<213> ORGANISM: Artificial Sequence
<220> FEATURE:
<223> OTHER INFORMATION: CA645 VH

<400> SEQUENCE: 1

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Asn Tyr Ala
            20                  25                  30

Ile Asn Trp Val Arg Gln Ala Pro Gly Lys Gly Leu Glu Trp Ile Gly
        35                  40                  45

Ile Ile Trp Ala Ser Gly Thr Thr Phe Tyr Ala Thr Trp Ala Lys Gly
    50                  55                  60

Arg Phe Thr Ile Ser Arg Pro Ser Thr Val Asp Leu Glu Met Thr
65                  70                  75                  80

Ser Leu Thr Thr Ala Asp Thr Ala Thr Tyr Phe Cys Ala Arg Thr Val
                85                  90                  95
```

```
Pro Gly Tyr Ser Thr Ala Pro Tyr Phe Asp Leu Trp Gly Pro Gly Thr
            100                 105                 110

Leu Val Thr Val Ser Ser
        115
```

<210> SEQ ID NO 2
<211> LENGTH: 119
<212> TYPE: PRT
<213> ORGANISM: Artificial Sequence
<220> FEATURE:
<223> OTHER INFORMATION: CA645 VH gH1

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Ser Thr Thr Val Tyr Leu Gln Met
65                  70                  75                  80

Asn Ser Leu Arg Ala Glu Asp Thr Ala Val Tyr Tyr Cys Ala Arg Thr
                85                  90                  95

Val Pro Gly Tyr Ser Thr Ala Pro Tyr Phe Asp Leu Trp Gly Gln Gly
            100                 105                 110

Thr Leu Val Thr Val Ser Ser
        115
```

<210> SEQ ID NO 3
<211> LENGTH: 121
<212> TYPE: PRT
<213> ORGANISM: Artificial Sequence
<220> FEATURE:
<223> OTHER INFORMATION: CA645 VH gH5

<400> SEQUENCE: 3

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120
```

<210> SEQ ID NO 4
<211> LENGTH: 121
<212> TYPE: PRT

<213> ORGANISM: Artificial Sequence
<220> FEATURE:
<223> OTHER INFORMATION: CA645 VH gH37

<400> SEQUENCE: 4

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Ala Tyr Ala Thr Trp Ala Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120
```

<210> SEQ ID NO 5
<211> LENGTH: 121
<212> TYPE: PRT
<213> ORGANISM: Artificial Sequence
<220> FEATURE:
<223> OTHER INFORMATION: CA645 VH gH47

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Ala Ala Pro Tyr Phe Asp Leu Trp Gly
            100                 105                 110

Gln Gly Thr Leu Val Thr Val Ser Ser
        115                 120
```

<210> SEQ ID NO 6
<211> LENGTH: 110
<212> TYPE: PRT
<213> ORGANISM: Artificial Sequence
<220> FEATURE:
<223> OTHER INFORMATION: CA645 VL

<400> SEQUENCE: 6

```
Ala Ala Val Leu Thr Gln Thr Pro Ser Pro Val Ser Ala Ala Val Gly
1               5                   10                  15

Gly Thr Val Thr Ile Asn Cys Gln Ser Ser Pro Ser Val Trp Ser Asn
            20                  25                  30
```

Phe Leu Ser Trp Tyr Gln Gln Lys Pro Gly Gln Pro Pro Lys Leu Leu
            35                  40                  45

Ile Tyr Glu Ala Ser Lys Leu Thr Ser Gly Val Pro Ser Arg Phe Lys
 50                  55                  60

Gly Ser Gly Ser Gly Thr Gln Phe Thr Leu Thr Ile Ser Asp Val Gln
65                   70                  75                  80

Cys Gly Asp Ala Ala Thr Tyr Tyr Cys Gly Gly Tyr Ser Ser Ile
                 85                  90                  95

Ser Asp Thr Thr Phe Gly Gly Gly Thr Lys Val Val Val Lys
                100                 105                 110

<210> SEQ ID NO 7
<211> LENGTH: 110
<212> TYPE: PRT
<213> ORGANISM: Artificial Sequence
<220> FEATURE:
<223> OTHER INFORMATION: CA645 VL gL1

<400> SEQUENCE: 7

Asp Ile Val Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
                20                  25                  30

Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Lys
 50                  55                  60

Gly Ser Gly Ser Gly Thr Asp Phe Thr Leu Thr Ile Ser Ser Leu Gln
65                   70                  75                  80

Pro Glu Asp Phe Ala Thr Tyr Tyr Cys Gly Gly Tyr Ser Ser Ile
                 85                  90                  95

Ser Asp Thr Thr Phe Gly Gly Gly Thr Lys Val Glu Ile Lys
                100                 105                 110

<210> SEQ ID NO 8
<211> LENGTH: 110
<212> TYPE: PRT
<213> ORGANISM: Artificial Sequence
<220> FEATURE:
<223> OTHER INFORMATION: CA645 VL gL4

<400> SEQUENCE: 8

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
                20                  25                  30

Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Ser
 50                  55                  60

Gly Ser Gly Ser Gly Thr Asp Phe Thr Leu Thr Ile Ser Ser Leu Gln
65                   70                  75                  80

Pro Glu Asp Phe Ala Thr Tyr Tyr Cys Gly Gly Tyr Ser Ser Ile
                 85                  90                  95

Ser Asp Thr Thr Phe Gly Gly Gly Thr Lys Val Glu Ile Lys
                100                 105                 110

```
<210> SEQ ID NO 9
<211> LENGTH: 110
<212> TYPE: PRT
<213> ORGANISM: Artificial Sequence
<220> FEATURE:
<223> OTHER INFORMATION: CA645 VL gL5

<400> SEQUENCE: 9

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Ala Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys
                100                 105                 110
```

UNITED STATES PATENT AND TRADEMARK OFFICE
CERTIFICATE OF CORRECTION

| | | |
|---|---|---|
| PATENT NO. | : 11,466,076 B2 | Page 1 of 1 |
| APPLICATION NO. | : 16/098085 | |
| DATED | : October 11, 2022 | |
| INVENTOR(S) | : Adams et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 564 days.

Signed and Sealed this
Fourth Day of February, 2025

Coke Morgan Stewart
*Acting Director of the United States Patent and Trademark Office*